(12) United States Patent  
Wachman et al.

(10) Patent No.: US 8,110,159 B2  
(45) Date of Patent: Feb. 7, 2012

(54) AOTF-BASED IMAGING SYSTEM AND METHOD FOR HYPERSPECTRAL AND MULTISPECTRAL IMAGING OF SPECIMENS INCLUDING MEDICAL TISSUE

(75) Inventors: Elliot S. Wachman, Lakewood, NJ (US); Jill Wachman, Lakewood, NJ (US); Stanley J. Geyer, Pittsburgh, PA (US)

(73) Assignee: Gooch and Housego PLC, Somerset (GB)

( * ) Notice: Subject to any disclaimer, the term of this patent is extended or adjusted under 35 U.S.C. 154(b) by 62 days.

(21) Appl. No.: 12/675,677

(22) PCT Filed: Sep. 2, 2008

(86) PCT No.: PCT/US2008/075058  
§ 371 (c)(1),  
(2), (4) Date: Feb. 26, 2010

(87) PCT Pub. No.: WO2009/029950  
PCT Pub. Date: Mar. 5, 2009

(65) Prior Publication Data  
US 2010/0246907 A1  Sep. 30, 2010

Related U.S. Application Data

(60) Provisional application No. 60/969,424, filed on Aug. 31, 2007.

(51) Int. Cl.  
*G02F 1/11* (2006.01)  
*A61B 10/00* (2006.01)

(52) U.S. Cl. .......... 422/536; 422/82.05; 422/82.06; 422/82.08; 422/82.09; 436/63; 436/172; 356/36; 356/303; 356/244; 359/285; 359/305; 359/578; 359/579; 435/288.3; 435/288.7; 382/128; 382/133

(58) Field of Classification Search .......... 422/82.05, 422/82.06, 82.08, 82.09, 536; 436/63, 172; 356/36, 303, 244; 359/285, 305, 578, 579; 435/288.3, 288.7; 382/128, 133  
See application file for complete search history.

(56) References Cited

U.S. PATENT DOCUMENTS

| | | | |
|---|---|---|---|
| 6,750,964 B2 * | 6/2004 | Levenson et al. | 356/326 |
| 7,283,290 B1 * | 10/2007 | Pannell et al. | 359/285 |
| 7,316,904 B1 * | 1/2008 | Farkas et al. | 435/6.14 |

* cited by examiner

*Primary Examiner* — Jill Warden  
*Assistant Examiner* — Monique Cole  
(74) *Attorney, Agent, or Firm* — Jetter & Associates, P.A.

(57) ABSTRACT

An imaging system includes a platform for placement of a sample or an animal to be imaged, and at least one excitation light source for irradiating the sample or animal to stimulate an emission at a plurality of different center wavelengths. An acousto-optic tunable filter (AOTF) is provided that includes a piezoelectric transducer crystal for emitting an acoustic wave having a ground electrode disposed on one side of the piezoelectric crystal. A patterned electrode layer is disposed on a side of the piezoelectric crystal opposite the ground electrode. The patterned electrode layer includes a continuous region proximate to its center and a discontinuous region, a pattern in the discontinuous region comprising a plurality of spaced apart features electrically connected to the continuous region, and an AO interaction crystal receiving the acoustic wave attached to the ground electrode or the patterned electrode layer.

7 Claims, 15 Drawing Sheets

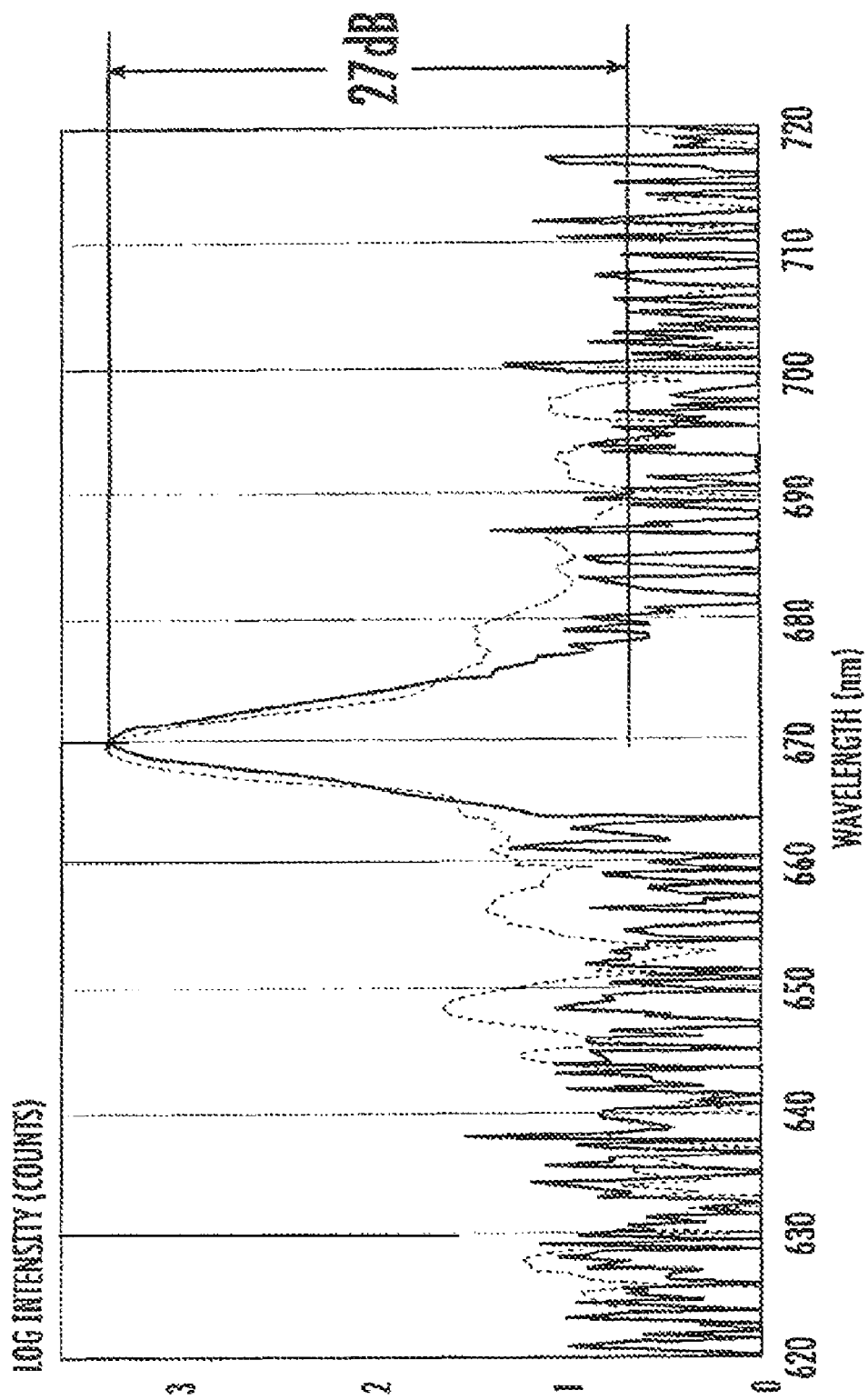

AOTF-BASED IMAGING SYSTEM AND METHOD FOR HYPERSPECTRAL AND MULTISPECTRAL IMAGING OF SPECIMENS INCLUDING MEDICAL TISSUE

CROSS REFERENCE TO RELATED APPLICATION

This application is a national stage application that claims priority to PCT/US/2008/075058 filed Sep. 2, 2008 which claims priority to provisional patent application 60/969,424 filed Aug. 31, 2007, both of which are incorporated herein in their entireties.

FIELD

Embodiments of the invention are directed to methods and an acousto-optical tunable filter (AOTF)-based imaging system for hyperspectral and multispectral imaging of specimens including medical tissue.

BACKGROUND

In making a diagnosis, pathologists often rely on preparation of the cytology or histopathology specimens being examined with one or a combination of several standard staining regimens. The most common of these are transmission stains (including Hematoxylin and Eosin (H&E) and PAP stains), immunohistochemical stains (DAB being the most common), and a variety of fluorescence probes targeted to proteins or structures outside of the nucleus, or to nucleic acid probes or genetic markers within the nucleus. As known in the art, H&E staining is one of the most common stains used in histology. This staining method involves application of the basic dye haematoxylin, which colors basophilic structures with blue-purple hue, and alcohol-based acidic eosin Y, which colors eosinophilic structures bright pink. There are numerous applications where it would be desirable to detect a plurality of (e.g. four or more) of these fluorescence probes within a single nucleus or cell in addition to being able to examine the morphology and architecture of the same specimen on the same histology slide using conventional transmission staining, such as H&E or pap.

Devices in which an acoustic beam and an optical beam interact are generally referred to as "acousto-optic devices" or AO devices. Certain AO devices are used for imaging. One example of an AO device for imaging is an AOTF. As well known in the art, the AOTF is a solid-state electronically tunable spectral bandpass filter, which operates on the principle of acousto-optic interaction in an anisotropic medium. The AOTF utilizes an anisotropic, birefringent AO medium for its operation. AOTFs are currently used in certain medical applications.

An AOTF is frequently used when it is desired to rapidly select one or more optical wavelengths from an incident optical beam containing a range of optical wavelengths. FIG. 1 shows the k-space diagram and accompanying real-space diagram for a typical non-collinear AOTF 100. The AOTF 100 shown includes a piezoelectric acoustic transducer t 105 bonded to a crystal of suitable birefringent AO interaction crystalline material 110 (PQWS in FIG. 1). The electrodes disposed on both sides of the transducer (t) 105 are not shown for simplicity. The phase velocity of the acoustic wave emerging from t is at an angle $\theta_a$ to the optical axis of the AO interaction crystal 110. Light enters the AOTF 100 through the input face RS of the AO interaction crystal 110 having incident polar angle $\theta$, and wave vector k. Provided the RF frequency applied is adjusted to satisfy the resonant condition, the light is strongly diffracted to emerge through the output face PQ of the AO interaction crystal 110 with the diffracted wave vector $k_d$, at a polar angle $\theta_d$. The angular distance between the incident light and the first order diffracted light is therefore $\theta_d-\theta$, allowing separation of the respective light beams.

If white or other broadband light is incident on the AOTF, then once the RF frequency (and hence the acoustic wavelength and acoustic k-vector $K_A$) is chosen, only a narrow band of optical wavelengths close to the resonant wavelength will be diffracted. Such a device may for example be used in a spectroscopic instrument or hyperspectral imaging system, where the input beam of unfiltered light corresponds to some part of the optical train, e.g. the "infinity space" of an optical microscope in which the angular divergence of the light collected from the object is purposely kept small. This infinity space is designed for the insertion of optical filters, polarizers and other components by the manufacturer. Although an optical microscope is used herein for the purposes of illustration, these comments apply equally well to any other optical imaging system. An AOTF has significant advantages for such an application because of its ability to tune very quickly between wavelengths. Typical non-collinear AOTFs made using $TeO_2$ use acoustic wavelengths in the range of 5 to 20 µm in the interaction medium. By applying more than one RF frequency simultaneously, multiple optical pass bands may be created, this being an advantage besides speed provided by an AOTF over competing technologies.

Since AOTFs were developed many years before interest in precision applications including imaging reached its present high levels, conventional AOTFs do not provide the performance required for more demanding applications. In precision applications it is important for the AOTF to allow through only light wavelengths that are in a narrow band centered on the selected wavelength, and strongly reject all other wavelengths.

A standard AOTF uses continuous electrodes on both sides of the transducer. Such a device generates a uniform acoustic field throughout the interaction length in the AO interaction crystal. This arrangement that is not conducive to either high quality image formation or good filter response. A uniform acoustic field produces an optical pass-band that has poor rejection of adjacent wavelengths owing to the presence of significant sidelobes in the transmission function of the filter. It is the height of these sidelobes relative to the height of the main filter peak, which to a large extent determines the overall performance of the AOTF.

FIG. 2 shows an AOTF 200 including a rectangular transducer electrode 210 and associated AO interaction crystal 215, along with the resulting acoustic field shown below in the AO interaction crystal 215. The area of electrode 210 defines the functional area of the generally larger area associated transducer (transducer not shown in FIG. 2). It is generally known to improve AOTF operation the acoustic intensity in the interaction region of the AO interaction crystal should start off at a low level at the input end of the interaction region, then build up smoothly to a maximum in the center of the interaction region (x=L/2 in FIG. 2). After the center the acoustic intensity should fall off so that it is again low at the output end of the interaction region. The exact form of the mathematical function, which defines the rise and fall of the acoustic amplitude, S(x) in FIG. 2, is not unique. Many "windowing functions" have been used in the context of Fourier transforming of data, for example, the Parzen window, the cosine window, the truncated Gaussian, and most are generally suitable.

The local strength of the acoustic wave generated by a piezoelectric transducer depends on the product of (1) the local electric field strength and (2) the local piezoelectric activity, the latter being related to the crystal structure of the transducer. Usually the transducer used in acousto-optic devices is a single crystal of lithium niobate (LN). A piezoelectric material such as LN is a so-called "hard ferroelectric" and it is difficult to manipulate the local piezoelectric strength in the way one may for example manipulate the local piezoelectricity of a piezoelectric ceramic. This latter material being typically used in acoustic transducers for generation of lower frequency (tens to hundreds of kHz) acoustic waves for example in sonar applications. Thus, it is relatively easy to arrange for a sonar transducer launching an acoustic beam into water to be apodized by controlling the degree of local poling of the piezoelectric material, and so generate an acoustic beam of arbitrary spatial intensity distribution. However, it is comparatively difficult to apodize the beam from a LN transducer launching an acoustic beam into an AO crystal. A designer generally has only two options in practice; to attempt alter the piezoelectric activity, or to locally alter the electric field strength.

Local alteration of the electric field inside the LN crystal comprising the acoustic transducer can be achieved by patterning the top electrode. Instead of a continuous top electrode of substantially rectangular form which is conventionally used, a pattern can be chosen which achieves a gradual reduction of the average electric field in the piezoelectric transducer with movement out towards the input and output faces of the acousto-optic interaction crystal, and thus generates some apodization of the acoustic wave. This has been achieved by dividing up the rectangular top electrode into a small number (e.g. up to 11) of electrically independent sub-electrodes and driving at least some of the electrodes using a multiplicity of independent RF drivers. In this arrangement, each electrode segment requires its own matching circuit and flexible cable connection to the multichannel "driver", the latter containing all the RF drive electronics including the RF amplifiers. All the cables must be closely matched in length to within a few mm and the adjustment procedure needed to get all the transducer sub-elements operating substantially in phase over the whole tuning range is difficult, requiring a high level of skill. If the transducer elements do not operate in phase due to incorrect adjustment or manufacture, the device will not work properly. The RF power fed to the transducer sub-elements is chosen to approximate to the desired apodization function, for example a Gaussian, the "tails" being at the input and output ends of the interaction region, and the maximum being in the center. This method generally works well when it is adjusted properly, and side-lobe reductions of 20 dB can be achieved, however it is complicated and expensive, requiring a complicated and expensive bank of RF drivers rather than a single RF driver.

It is a known peculiarity of the AOTF that the spatial resolution, as well as the spectral resolution, is determined by the spectral sidelobe rejection within the AOTF. The quality the imaging provided by the AOTF thus generally relates to the magnitude of the sidelobes transmitted along with the beam of interest.

Regarding pathology, a pathologist now generally requires a separate tissue section or cytology specimen for each target to be examined with a fluorescence probe, and an additional specimen for the transmission stain examination. Examination of these numerous slides serve as multiple adjuncts for the pathologist in making the final diagnosis. What is needed is a new AOTF design that strongly shapes or "apodizes" the acoustic beam to optimize filter quality and image quality by substantially reducing the level of the undesired sidelobes transmitted with the desired optical beam. An AOTF-based system providing sharply reduced side lobes would permit simultaneously imaging a plurality fluorescent or transmission tags, such as samples prepared with both a transmission stain and numerous fluorescence markers, for improved hyperspectral and multispectral imaging of medical tissues. Such a system would allow all these tests to be performed on a single slide with a single sample, thereby minimizing the amount of tissue required, avoiding artifacts resulting from the use of different parts of the tissue being used for each slide, and simplifying and speeding-up interpretation by the pathologist.

SUMMARY

This Summary is provided to comply with 37 C.F.R. §1.73, presenting a summary of this Disclosure to briefly indicate the nature and substance disclosed herein. It is submitted with the understanding that it will not be used to interpret or limit the scope or meaning of the claims.

An imaging system according to an embodiment of the invention comprises a platform for placement of a sample or an animal to be imaged, at least one excitation light source for irradiating the sample or animal to stimulate a response comprising emission at a plurality of different center wavelengths. An AOTF comprises a piezoelectric transducer crystal for emitting an acoustic wave having a ground electrode disposed on one side of the piezoelectric crystal. A patterned electrode layer is disposed on a side of the piezoelectric crystal opposite the ground electrode, the patterned electrode layer including a continuous region proximate to its center and a discontinuous region, a pattern in the discontinuous region comprising a plurality of spaced apart features electrically connected to the continuous region, and an AO interaction crystal for receiving the acoustic wave attached to the ground electrode or the patterned electrode layer.

The feature sizes of the features in the pattern are sufficiently small to provide a fine structure far field condition for the acoustic wave in the AO interaction crystal underlying the discontinuous region beginning <10 mm measured from an interface between the piezoelectric crystal and the AO interaction crystal. A radio frequency (RF) power supply provides a variable RF frequency coupled across the electrodes for tuning a transmission wavelength of the AOTF. An image sensor is coupled to receive the emission transmitted by the AOTF. Systems according to disclosed embodiments enable the qualitative and quantitative imaging of samples prepared with both a transmission stain and numerous different fluorescence markers.

BRIEF DESCRIPTION OF THE DRAWINGS

A fuller understanding of subject matter disclosed herein and the features and benefits thereof will be obtained upon review of the following detailed description together with the accompanying drawings, in which:

FIG. 3(a) shows a top electrode in the form of a "diamond" shape, which has been used to achieve apodization of the acoustic wave field, while

DETAILED DESCRIPTION

Figure 1:
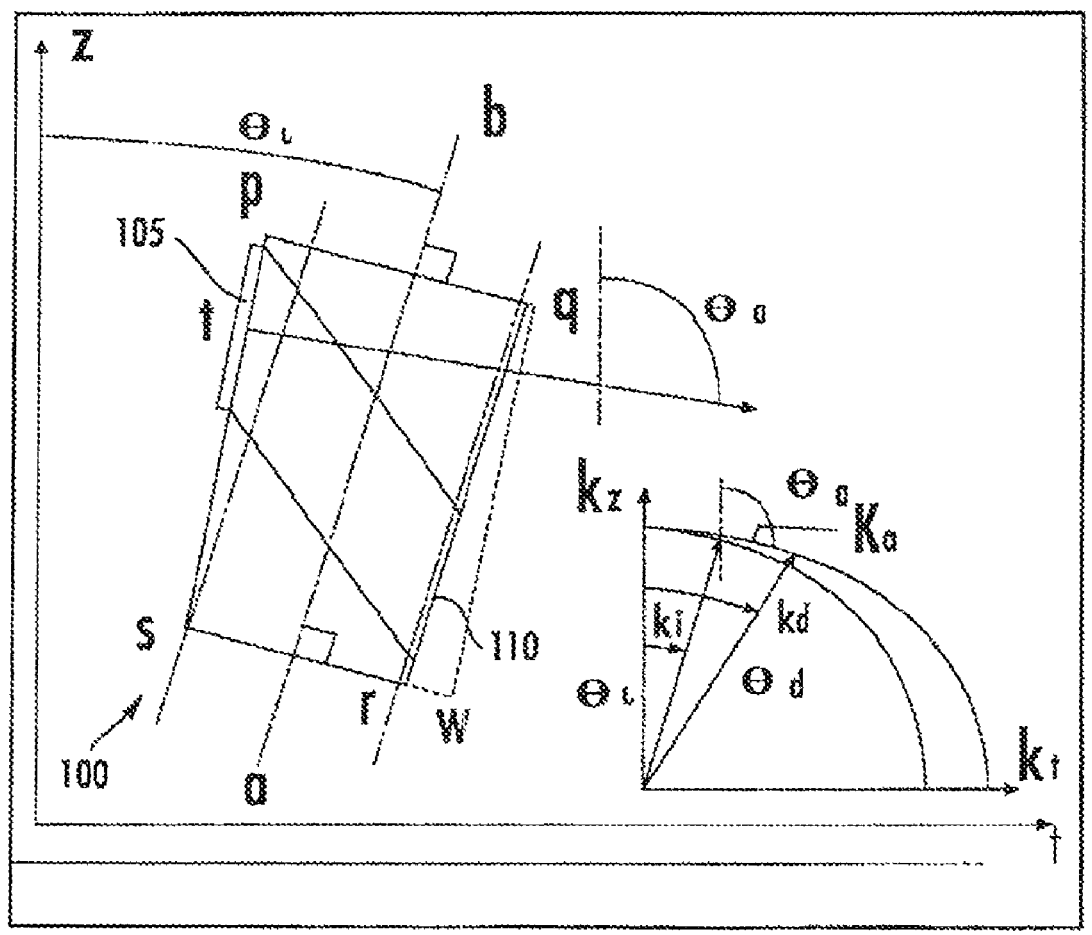
FIG. 1 shows a schematic of a conventional non-collinear AOTF showing a piezoelectric transducer bound to an AO interaction crystal. The accompanying associated k-vector diagram explains the operation of the AOTF.

Disclosed embodiments are described with reference to the attached FIGs., wherein like reference numerals are used throughout the FIGs. to designate similar or equivalent elements. The FIGs. are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. Embodiments of the invention are not limited by the illustrated ordering of acts or events, as some acts may occur in different orders and/or concurrently with other acts or events. Furthermore, not all illustrated acts or events are required to implement a methodology in accordance with this Disclosure.

As noted in the background above, the spatial resolution of an AOTF, as well as its spectral resolution, is primarily determined by the spectral sidelobe rejection within the AOTF since the quality of the AOTF generally relates to the magnitude of the sidelobes transmitted along with the beam of interest. Disclosed embodiments include an AO device having a patterned electrode layer including a continuous region proximate to its center and a discontinuous region, where a pattern in the discontinuous region comprising a plurality of spaced apart features electrically connected to said continuous region. The feature sizes of the features in the pattern are sufficiently small to provide a fine structure far field condition for said acoustic wave in said AO interaction crystal underlying the discontinuous region beginning <10 mm measured from an interface between said piezoelectric crystal and said AO interaction crystal.

Electrode patterns disclosed herein significantly have been found to provide low sidelobe levels of generally between −20 and −30 dB relative to the main peak across an operating band as demonstrated in the Examples below. In FIGS. 10-12 (described in the Examples section), the average for all measurements was a sidelobe level of −27.5 dB relative to the main peak for optical wavelengths spanning most of the visible light range.

AOTFs according to embodiments of the invention thus strongly apodize the acoustic beam to optimize filter quality and image quality by substantially reducing the level of the undesired sidelobes transmitted with the desired optical beam. An AOTF-based system providing sharply reduced side lobes permits simultaneously imaging that previously required multiple images and multiple samples. For example, AOTF-based systems according to embodiments of the invention permit simultaneously imaging a plurality fluorescent or transmission tags, such as samples prepared with both a transmission stain and numerous different fluorescence markers, which permits improved hyperspectral and multispectral imaging of medical tissues. Such systems allow all these tests, such as multiple fluorescence tagging of diagnostically relevant proteins together with H&E transmission stain, to be performed on a single slide with a single sample, thereby minimizing the amount of tissue required, avoiding artifacts resulting from the use of different parts of the tissue being used for each slide, and simplifying and speeding-up interpretation by the pathologist.

An imaging system according to an embodiment of the invention comprises a platform for placement of a sample or an animal to be imaged, at least one excitation light source for irradiating the sample or animal to stimulate a response comprising emission at a plurality of different center wavelengths. An acousto-optic tunable filter (AOTF) comprises a piezoelectric transducer crystal for emitting an acoustic wave having a ground electrode disposed on one side of the piezoelectric crystal. A patterned electrode layer is disposed on a side of the piezoelectric crystal opposite the ground electrode, the patterned electrode layer including a continuous region proximate to its center and a discontinuous region, a pattern in the discontinuous region comprising a plurality of spaced apart features electrically connected to the continuous region, and an AO interaction crystal receiving the acoustic wave attached to the ground electrode or the patterned electrode layer. The feature sizes of the features in the pattern are sufficiently small to provide a fine structure far field condition for the acoustic wave in the AO interaction crystal underlying the discontinuous region beginning <10 mm measured from an interface between the piezoelectric crystal and the AO interaction crystal. A radio frequencies (RF) power supply provides a variable RF frequency coupled across the electrodes for tuning a transmission wavelength of the AOTF. An image sensor is coupled to receive the emission transmitted by the AOTF.

Figure 4:
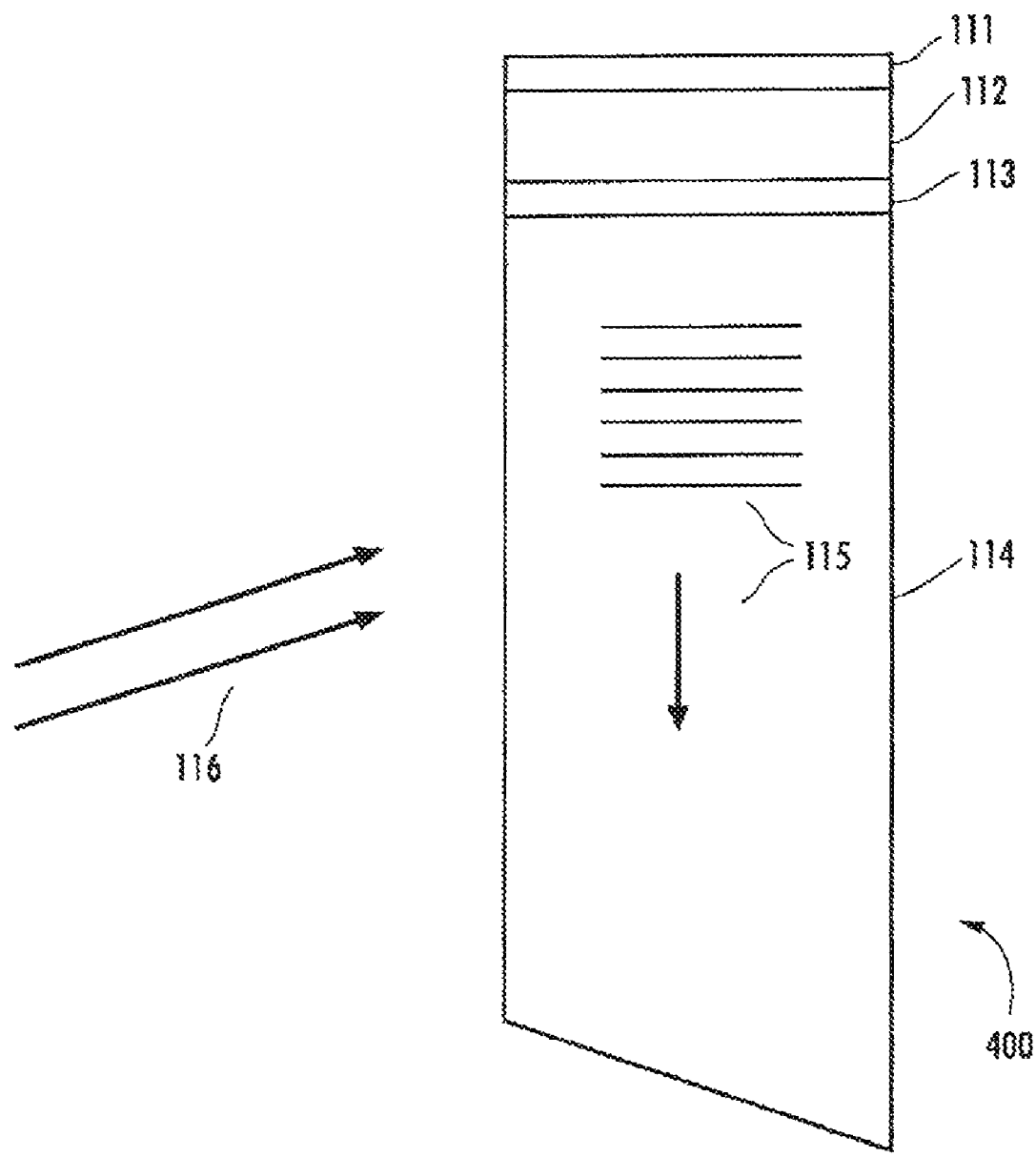
FIG. 4 shows a side view of an acousto-optic AO device for generating a highly apodized acoustic wave, according to an embodiment of the invention.

FIG. 4 shows a side view of an acousto-optic (AO) device 400 used in AOTFs according to an embodiments of the invention. AO device 400 generates a highly apodized acoustic wave and comprises an AO interaction crystal 114, piezoelectric material 112, top electrode(s) 111 and bottom electrode(s) 113. The AO interaction crystal 114 is a birefringent material in certain applications, such as when the device is an AOTF. One of the electrodes is a patterned layer having "fine structure" and the electrodes 111 and 113 are separated by the thickness of the piezoelectric material 112. The patterned electrode layer includes a continuous region proximate to its center (midpoint of the interaction length) and a discontinuous region on both sides of the center, as will be described in detail below together with exemplary patterns shown in several FIGs. The pattern in the discontinuous region comprises a plurality of spaced apart features electrically connected to the continuous region.

Sound waves, represented by lines and arrow 115, are generated by piezo-electric material 112 in response to RF signals applied across top electrode 111 and bottom electrode 113. Arrows 116 represent incident optical beams being transmitted toward AO crystal 114. The index of refraction throughout AO crystal 114 varies based on the sound waves generated by piezo-electric material and propagated through AO crystal 114. The sound waves control what portion of the incident optical beams are diffracted as the optical beams travel through AO crystal 114. The shape of the electrodes in the patterned electrode layer influences the shape of sound waves propagating through AO crystal 114 and is generally the focus of the principal embodiments of the invention.

The feature size(s) of the features in the electrode pattern referred to herein as being a "fine structure" is sufficiently small to provide a fine structure far field condition (as defined below) for the acoustic wave in the AO interaction crystal underlying the discontinuous region beginning <10 mm measured from an interface between the piezoelectric crystal and the AO interaction crystal for a 10 micron wavelength acoustic wave. When fine structure far field condition distances are specified herein, the acoustic wavelength is at 10 microns, unless otherwise noted. Acoustic waves in the range from 5 to 20 microns represents a typical design tuning range for a non-collinear AOTF operating in the visible or near-IR portions parts of the electromagnetic spectrum). For example, constraining the desired far field associated with the fine structure to begin <5 mm away from the piezoelectric/AO interaction crystal interface, equation 1 (described below) with $Z_0$=5 mm gives L=158 microns for an acoustic wavelength, $\Lambda$=5 microns, and L=224 microns for an acoustic wavelength of 10 microns. If the maximum allowable characteristic feature size in the top electrode pattern is taken to be the minimum of 158 and 224, i.e. 158, the desired condition on the far field will be satisfied throughout the full tuning range of the device.

In devices actually fabricated, electrode patterns have been on the order of 10× finer than this maximum feature size, because mask patterns were generated on a (10 micron by 10 micron) grid, resulting in characteristic features sizes of the order of 10 microns in the patterns generated. Thus, according to equation 1, the fine structure far field is calculated to begin only 10 microns (0.01 mm) away from the interface in the case of 10 micron acoustic waves, and only 20 microns (0.02 mm) away in the case of 5 micron acoustic waves, thus, for generally all practical purposes, at the interface itself.

The numerical factor $\xi$ which appears in equation 1 is related to the curvature of the acoustic dispersion surface and a modification introduced to take account of the fact that the material is acoustically anisotropic. For $TeO_2$, and in similar materials for non-collinear AOTFs, $\xi$ is less than unity, for example, 0.2, which for a given characteristic feature size L, and a given wavelength, $\Lambda$ in equation 1, results in a reduction of the Rayleigh range $Z_0$, compared to an isotropic material in which $\Lambda$ is unchanged. This actually benefits the inventive devices since it results in the fine structure far field region starting even closer to the interface than would be the case in an isotropic medium and so represents an added "safety factor" in the design.

Embodiments of the invention thus manipulate the electric field in the transducer using fine-structuring of an electrode layer associated with the transducer, in order to achieve high levels of apodization of the radiated acoustic field into the attached AO interaction crystal. Another related technique for achieving the desired fine structure far field condition for the acoustic wave in the AO interaction crystal involves locally altering the transducer crystal as described below. Both techniques may be combined. The high level of apodization obtained using either technique results in a far field condition for the acoustic wave in the AO interaction crystal to begin <10 mm of the transducer/AO crystal interface, such as <5 mm. Thus, embodiments of the invention keep almost the entire volume of the AO crystal in the far field of the top electrode fine structure. Electrode designs disclose herein have demonstrated side lobe levels for optical beams outputted by the devices according to embodiments of the invention reduced by 10-20 dB, or more, as compared to conventional rectangular electrode designs.

It is well known in diffraction theory that the sound wave field produced by a radiating acoustic transducer may be broadly divided into two distinct regions, (1) the near field and (2) the far field. The near field is characterized by relatively complex and inhomogeneous spatial phase and amplitude distributions, resulting in the phases and amplitudes which vary strongly with position. The far field is the region where the disturbance has traveled sufficient distance for the inhomogeneous phase distributions to have settled down into a much more orderly form. It is the onset of the region where the asymptotic properties of the wave field begin to show themselves, with the wave field beginning to display increased smoothness, and taking on characteristics of the familiar inverse square property.

The distinction between these two regions, the near and far field, is made herein and quantified with the aid of the so-called Rayleigh range $Z_0$, defined as:

$$Z_0 = \frac{\xi L^2}{\Lambda} \tag{1}$$

In equation (1) Zo is the Rayleigh range, often called the confocal parameter, L is a characteristic length associated with the transducer, $\xi$ is a numerical factor of the order unity, and $\Lambda$ is the acoustic wavelength. If the distance of interest $Z>Z_0$, far field conditions exist, otherwise near field conditions exist. The factor $\xi$ may be calculated once the exact geometry of the particular case is known, (e.g., see A. P. Goutzalis, "Design and Fabrication of Acousto-optic Devices", Publisher: CRC (Jan. 6, 1994) ISBN: 082478930X).

In a conventional non-apodized (uniform) AOTF transducer in which a rectangular top-electrode is used of dimension typically 10 mm square, at an acoustic wavelength of 10 μm (a typical figure), the value of the Rayleigh range $Z_0$ would be $Z_0=10$ m taking $\xi=1$ and L=10 mm (using equation 1). In the case of sonar or similar applications, a typical device having a transducer diameter of 50 mm operating at a frequency of 40 kHz (corresponding to an acoustic wavelength in water of 37 mm assuming an acoustic velocity of 1.48 km/sec in water) has a corresponding Rayleigh range $Z_0$ of approximately 68 mm. Since it is unlikely to use sonar to detect objects closer than 68 mm, such a device is always operating in the far field. However, in acousto-optics, the device unlike the sonar device includes an AO interaction crystal bonded to the transducer. The AO interaction crystal has characteristic sizes of a few cm generally being the upper limit due to the current state of the art of crystal growth. Accordingly, acousto-optic devices such as AOTFs are almost always operating in the near field of the transducer taken as a whole.

Figure 3A:
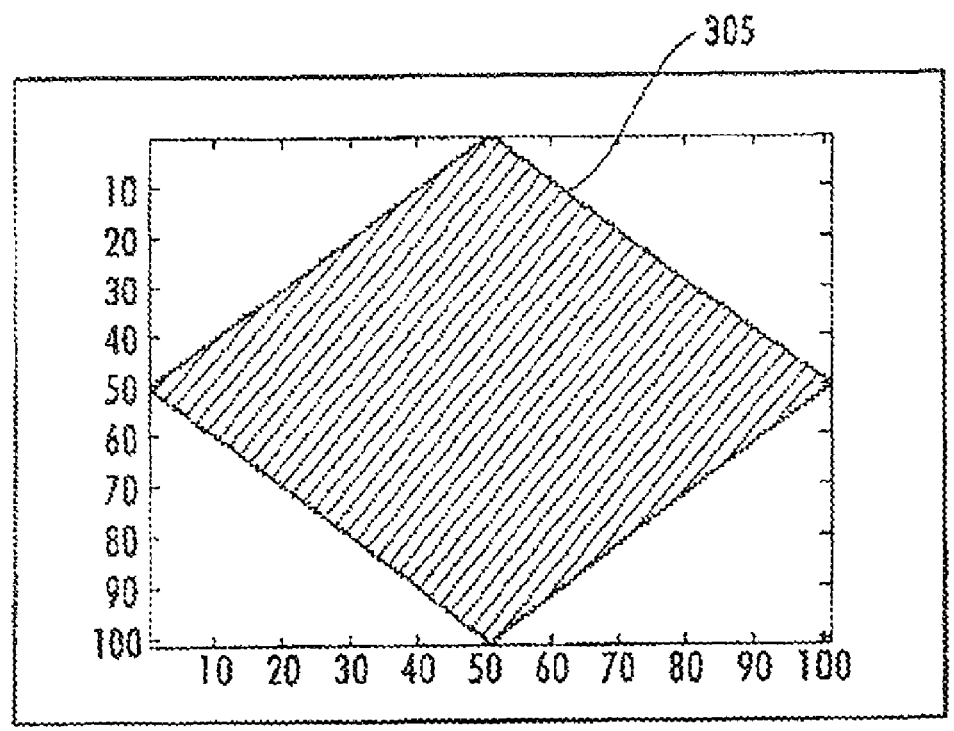
Figure 3B:
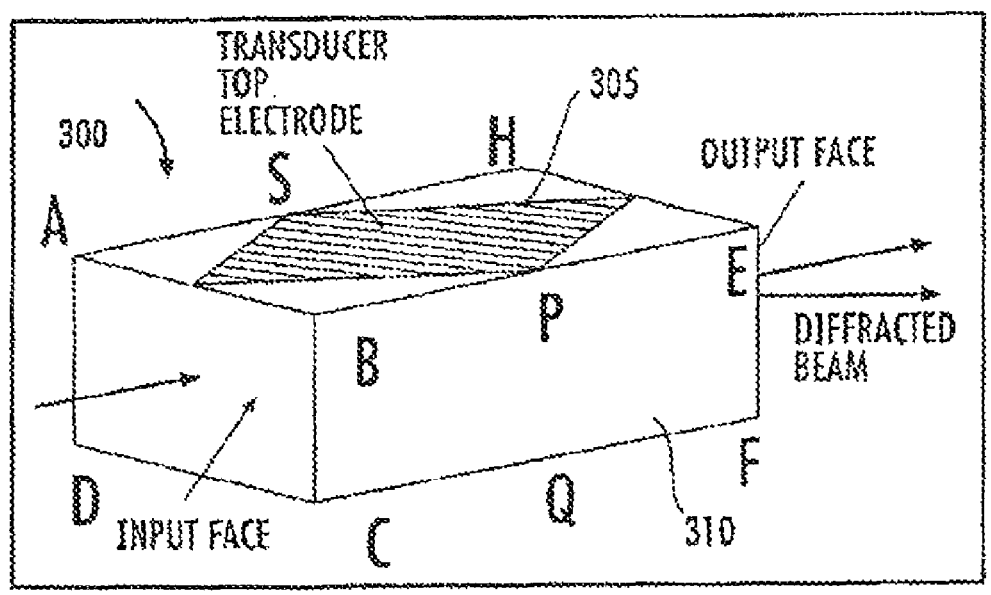
FIG. 3(b) shows the implementation of the transducer wherein light is incident on the AO interaction medium through the surface ABCD on its input face and exits through HEF on its output face.

The Inventors have found that if a metal electrode on the acoustic transducer is finely patterned to weaken the acoustic field radiated from some regions of the transducer, then the inhomogeneity in the radiated acoustic field caused by the patterning essentially vanishes at very small distances in the AO interaction crystal measured from the transducer interface. Referring now to FIGS. 3(a) and 3(b) that show a typical AOTF, because in a typical AOTF it is desirable for the useable optical aperture (i.e. the area of face ABCD in FIG. 3(b) to be as large as possible for a given crystal size, it is desired to typically want the useable optical aperture to extend from the far side DCQF to within a few mm from the crystal face on which the transducer is bonded (face ABEH in FIG. 3(b)).

To provide the desired apodization by patterning the metal top electrode, the characteristic length scale associated with that patterning (referred to below as $L_{apo}$) is generally small enough for the far field of the apodization fine structure given by:

$$Z_{apo} = \frac{\xi L_{apo}^2}{\Lambda} \quad (2)$$

to begin <10 mm, such as <5 mms from the transducer interface with the AO interaction crystal. It has be found by the Inventors that failure to fulfill this condition, for example by using an apodization scheme that is too coarse, results in the field inhomogeneity caused by the apodization scheme to propagate for large distances and still be evident in the region of the AO interaction crystal in which the acousto-optic interaction occurs. As a result, large amplitude and phase fluctuations in the radiated field introduced by the apodization scheme will not have been filtered or "smoothed" sufficiently and the apodization scheme will not work properly. This is the case with the AOTF device 300 shown in FIG. 3(b), in which substituting a diamond shaped top electrode instead of the rectangular electrode covering face ABEH represents an attempt at apodization, which is illustrative of a technique which can be considered to be macroscopic patterning, to distinguish it from the distinct fine patterning as disclosed herein.

It would be reasonable to define the characteristic length scale associated with this (macroscopic) apodization scheme to be $L_{apo}=L/2$ where L was the original length of side BE. Macroscopic patterning is defined here as any top electrode patterning which deviates from a uniformly metalled ("non-patterned") top electrode by the introduction of structure with a characteristic length scale which is the same order of magnitude as the original dimensions of the uniformly metalled region (usually rectangular). The device 300 of FIG. 3(b) having a diamond shaped top electrode is one example of this macroscopic patterning. The far field of the macroscopic apodization structure begins at one quarter of the Rayleigh range of the transducer as a whole in this case, i.e.

$$Z_{apo} = \frac{Z_0}{4} \quad (3)$$

In the previous calculated example described above, the Rayleigh range $Z_0$ of the transducer was 10 m, the Rayleigh range associated with the macroscopic structure is 2.5 m, still far too long for an acousto-optic device, for example, using an AO crystal of characteristic dimensions of the order of 3 cm. Using equation (1), if the Rayleigh range (Zo) of the apodization fine structure, $Z_{apo}$, is desired to be 5 mm, for example, then the maximum "characteristic length" of any top electrode feature appearing will be approximately 158 μm assuming an acoustic wavelength of 5 μm. Feature sizes can be defined by the smallest feature dimension, elected from features size (e.g. finger width) or feature spacing or feature repeat distances, in the case of periodic, or partly periodic patterns. Keeping to this selected fine electrode structure condition ensures that the region of acousto-optic interaction provided begins <5 mm from the transducer. As a result, operation of the AO device in this range will be safely in the far field of the transducer top electrode's fine structure.

Accordingly "fine patterning" as disclosed herein can be defined as the maximum allowable feature size in the discontinuous region of the pattern which provides a fine structure far field ($Z_{apo}$) beginning <10 mm of the interface between the transducer and AO crystal, in one embodiment <5 mm, in another embodiment <2.5 mm, and in yet another embodiment <1 mm, such as <0.5 mm, according to equation 2.

Alternatively, the "fine structure" can be defined as being on the same order of magnitude as the typical acoustic wavelengths in the device. For typically acoustic wavelengths in the 5-10 μm range, fine structure would thus mean feature sizes under 100 μm. More broadly, fine structure would be provided by dimensions within two orders of magnitude of the acoustic wavelength being processed, or <1,000 μm (1 mm) for a 10 μm acoustic wavelength.

This fine electrode structure for achieving apodization in acousto-optic devices principle is fundamental to embodiments of the invention. However, there is another principle believed to be operating which may also be considered, which has its origin in the need for the acoustic transducer to operate over a broad band of RF frequencies, typically an octave or more. In order to ensure a uniform ("flat") response of the filter over its design tuning range, it is important that the acoustic transducer does not radiate any sub-interval of acoustic wavelengths within the tuning range significantly more efficiently than any other. It is also important that the form of the apodization function is essentially independent of the acoustic wavelength in the range of interest (e.g. 5 μm to 10 μm), otherwise, in the case of the AOTF, the filter band shape and sidelobe levels will vary substantially as the device is tuned over a band. There are two ways to simultaneously achieve both conditions.

(1) One way is to make the characteristic length scales of the apodization fine structure comparable with, or smaller than, the smallest acoustic wavelength to be used, or (2) to arrange to have a distribution of characteristic length scales which is substantially uniform over the design tuning range (aperiodic condition). In other words, if the design tuning range of acoustic wavelengths is 5 μm to 10 μm, then fundamental feature sizes of substantially less than 5 μm should ideally be used in order to satisfy (1), or the pattern can be of a type that there was a uniform distribution of characteristic features sizes extending at least from 5 μm to 10 μm. Such a condition could be achieved by using an approximation to a fractal electrode metallization pattern, because a characteristic of a fractal pattern is that features are repeated or nearly repeated on a wide distribution of size scales. A definition of fractals, consistent with common usage, can be found in "Chaos and Fractals" by Heinz-Otto Peitgen, Hartmut Jürgens, Dietmar Saupe, Springer_verlag, 1992, 2004, ISBN 0-387-20229-3 (hereafter "Peitgen").

In another embodiment of the invention, the local piezoelectric activity is manipulated to achieve apodization of the radiated acoustic field. In an acoustic transducer which is bonded to some substrate, the strength of the acoustic wave generated in the substrate depends on the local electric field and the local piezoelectricity, more precisely, the product of the two. Varying either the local electric field as describing above is one way of doing this, and varying the local piezoelectric activity is another. As noted above, both variations can be used together to likely provide higher levels of apodization as compared to one variation.

One way to alter the local piezoelectric activity is by focusing laser (or other suitable radiation) radiation into the interior of the material so as cause local damage or depolarization of the crystal, thus lowering or eliminating the piezoelectric activity in that region. Focus generally results in the damage occurring in the bulk (rather than the surface) of the crystal. If this process of inducing damage sites is conducted on a fine enough scale, using the same rules for definition of fine structure as described above, then the required apodization will be produced. In this case, the "fine patterning" refers to the variations in local density of the damage sites in the transducer crystal. Regions of high density of damage generate low acoustic intensity, while regions which are undamaged by the radiation processing generate high acoustic intensity. The variations from place to place inside the transducer crystal conform to the rules of "fine patterning" as described above regarding electrode fine structure patterning. The variations in area density of damage sites can exceed the characteristic size of 100 μm so that the far field of the acoustic wave resulting from this fine patterning begins at <5 mm from the transducer interface with the AO crystal as in the case of top electrode fine patterning.

Figure 5:
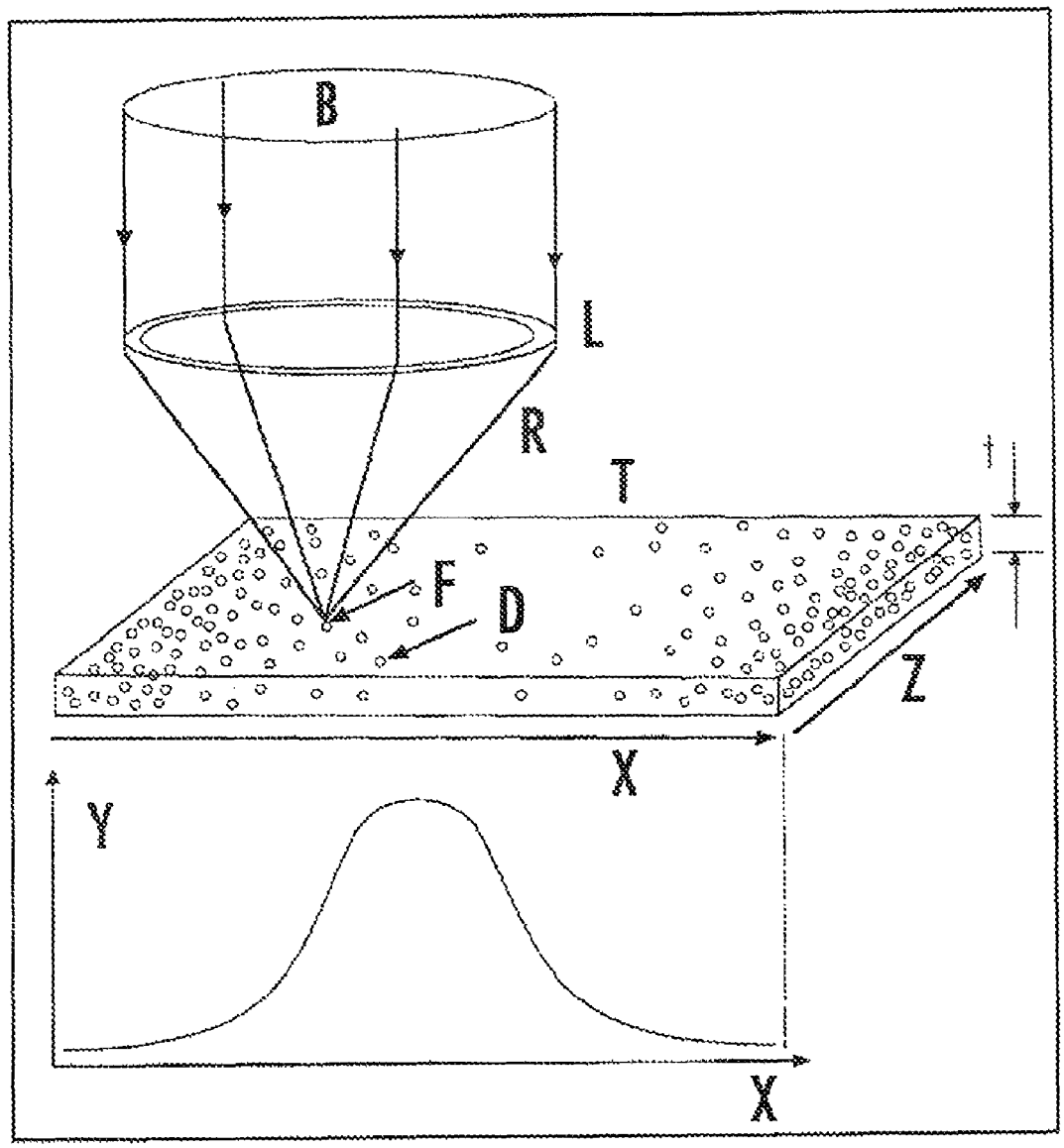
FIG. 5 shows an alternative apodization scheme in which laser radiation is used to alter the local piezoelectric activity of an initially homogeneous transducer crystal, according to an embodiment of the invention.

In this apodization scheme, as shown in FIG. 4, the electric field is uniform but the local piezoelectric activity of the piezoelectric (e.g. lithium niobate (LN)) is modified during manufacture using laser radiation. Using optical pulses of short duration (typically from 50 fs to several ns) the initially homogeneous plate of LN can be treated so as to change the local piezoelectric activity in chosen regions. FIG. 5 shows the density of modified sites being essentially random but the area density increasing on average towards the edges in a pre-arranged fashion to produce the desired apodization.

Figure 2:
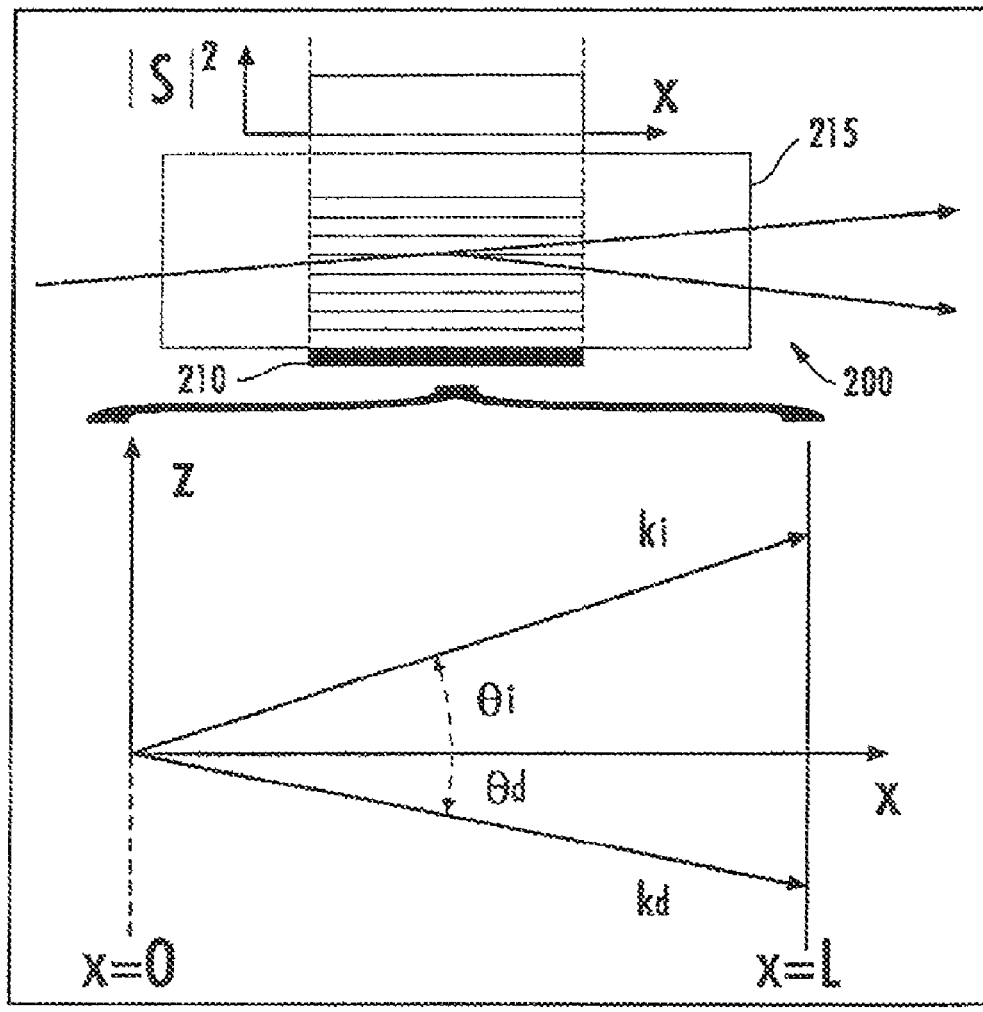
FIG. 2 shows schematically the effect on the sound intensity distribution in the AO interaction crystal of having a uniform acoustic transducer top electrode.

As shown in FIG. 5, the laser radiation, in the form of a beam B, can be focused onto the LN or other suitable transducer crystal T of thickness t, using a lens L of high numerical aperture. The laser radiation is typically be in the form of short pulses derived (e.g.) from a Ti:Sapphire laser, or may be a UV laser chosen to have a high absorption in LN. A computer driven translation stage (not shown) can be used to move the plate relative to the focal region of the laser radiation in both the x and y directions. As the pulse repetition rate of the type of mode-locked laser is typically in the range –kHz to hundreds of kHz, this procedure can be accomplished in a relatively short time making this method suitable for a production environment. The number density of the modified sites D appearing at the focus F will then depend on the amount of time that the particular region spends near the focus. The insert in FIG. 5 shows schematically the relative acoustic intensity (Y) averaged across the z-direction, as a function of x. In operation this LN transducer plate is bonded onto the AO crystal using industry standard techniques with x corresponding to the direction of optical propagation (as per FIG. 2).

The laser radiation when focused into the small regions shown in FIG. 5, will either reduce the piezoelectric activity or induce ferroelectric domain inversion. Either effect will serve to carry out the necessary apodization. It is also possible to influence the ability of the transducer to radiate efficiently by implanting regions of damage or alteration which represent mechanical inhomogenieties, these will serve as centers of acoustic Rayleigh scattering and so weaken the locally emitted acoustic wave by scattering it.

Figure 6:
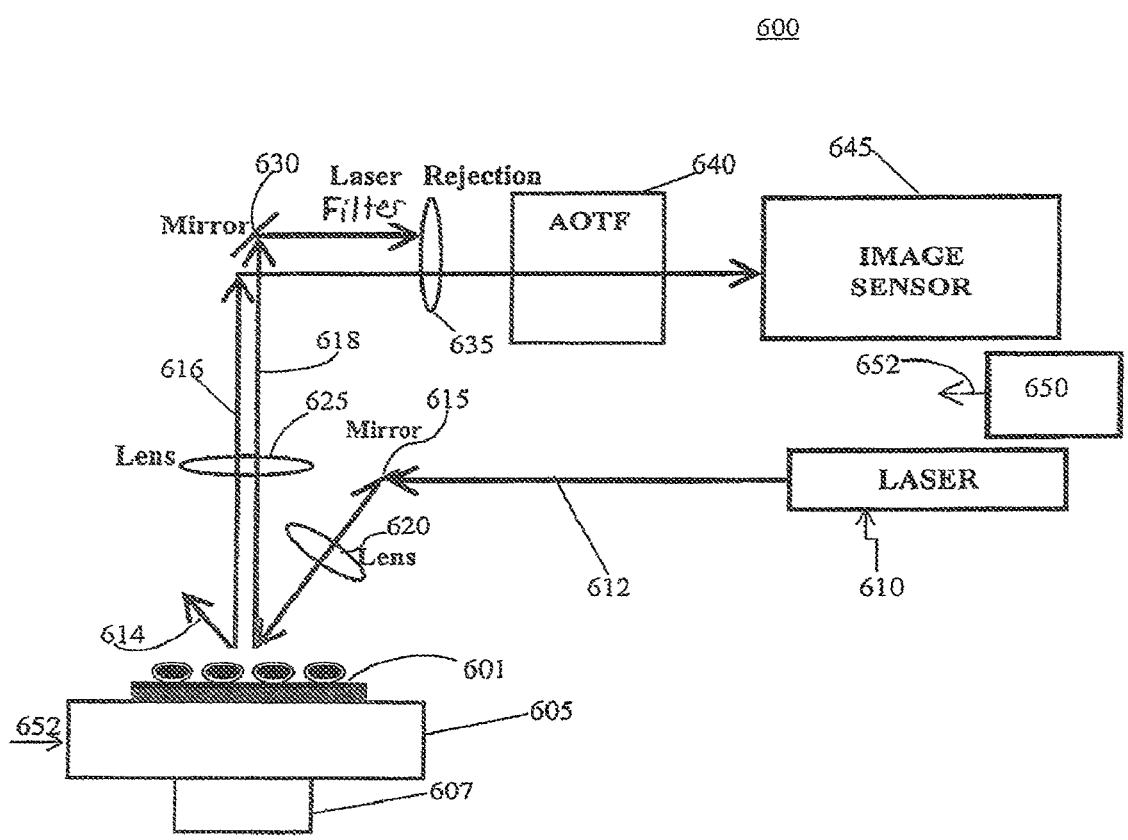
FIG. 6 schematically illustrates an exemplary AOTF-based imaging system for imaging samples on a platform, according to an embodiment of the invention.

FIG. 6 schematically illustrates an exemplary AOTF-based imaging system 600 according to an embodiment of the invention. A sample 601 is positioned on platform 605. Sample 601 may be any sample containing light absorbing material, including cells, tissue or live animals that are either unstained, prepared with one or more transmission stains, prepared with one or more transmission tags, or any combination of the above. Sample 601 may be an unknown sample for which a user would like to classify its disease state. Sample 601 can include a variety of samples such as tissue, tissue microarray, protein microarray, DNA microarray, and western blot. The sample can comprise tissue which includes kidney tissue, prostate tissue, lung tissue, colon tissue, bone marrow tissue, brain tissue, red blood tissue, breast tissue or cardiac muscle tissue.

Platform 605 has a section for at least one sample and a section which is generally devoid of the sample. Platform 605 is responsive to programmable code 652 which controls the motion of the platform sections relative to an optical lens 625. The programmable code 652 instructs a processor or controller 650 to move the platform 605 in the x, y or z directions in such a manner to position the section of the platform 605 that contains a sample out of the field of view of optical lens 625. The x, y or z directions are performed in the reverse direction to return the platform to the position where the sample 601 is in the field of view of optical lens 625.

System 600 includes a broadband light source, such as white light source 607, located under the sample 601. Light source 607 illuminates sample 601 with a plurality of photons which are either generally absorbed by the sample or transmitted through the sample.

System 600 optionally includes a substantially monochromatic light source 610 which is positioned to provide incident light to sample 601. Light source 610 can include any conventional photon source, including laser, LED, and other visible, IR or near IR source, including tunable sources. Light source 610 may also be selected to provide evanescence illumination of the sample. In one embodiment, the line width of the light source 610 is in the range of about 15-25 cm$^{-1}$.

Monochromatic light source 610 shown as a laser is positioned to provide incident light along a first optical path, which is at an angle to sample 601 as opposed to light shining orthogonal to sample 601. In other words, the radiation used to illuminate the sample need not pass through the optical train of a conventional microscope (or macroscope); rather, it can illuminate the sample at an oblique angle from above or below sample 601. Photon beam 612 is received and deflected by mirror 615 through lens 620. Lens 620 may optionally be used to focus the light on sample 601. Alternatively, the photon beam 612 may be directed towards the sample 601 without the need for the mirror 615.

The plurality of photons in beam 612 reaching sample 601 illuminate the sample 601 and are either scattered or emitted or absorbed from different locations on or within the sample, which can result in subsequent emission (luminescence) at different wavelengths. As known to those skilled in the art, the term "luminescence" includes a wide range of optical processes described using other names. These processes include: fluorescence, phosphorescence, photoluminescence, electroluminescence, chemiluminescence, sonoluminescence, thermoluminescence and even upconversion.

Optical lens 625 functions to collect transmitted photons represented by photon beam 616. Laser Light reflected by sample 601 towards minor 630 is shown as beam 618. Optical lens 625 may be used for collecting and focusing received photon beams. This includes gathering and focusing both polarized and the un-polarized photons. In general, the sample size determines the choice of light gathering optical lens 625. For example, a microscope lens may be employed for analysis of the sub-micron to micrometer specimens. For larger samples, macro lenses can be used. Optical lens 625 (as well as lens 620) may include a simple reduced resolution/ aberration lens with a larger numerical aperture to thereby increase the system's optical throughput and efficiency. Mirror 630 is positioned to direct transmitted photon beam 616 to AOTF 640. It should be noted that placement of mirror 630 is optional and may be unnecessary in configurations where AOTF 640 is positioned above sample 601. Filter 635 is provided to block the reflected laser beam 618 from reaching AOTF 640 while passing the desired photon beam 616.

System 600 includes an AOTF 640 for separating the collected photons into a plurality of wavelengths. AOTF 640 functions to sequentially pass, the transmitted photons, into a plurality of predetermined wavelength bands which are detected by image sensor 645. The plurality of predetermined wavelength bands include specific wavelengths or ranges of wavelengths. In one embodiment of the invention, the predetermined wavelength bands include wavelengths characteristic of the sample undergoing analysis. The AOTF may be selected to operate in one or more of the following spectral ranges: the ultraviolet (UV), visible, near infrared, and mid-infrared.

Although generally described for imaging fluorescence signals and absorption mode, disclosed embodiments may also be practiced using Raman, such as SERS, which is well known to require a microstructured or nanostructured coating of a suitable metal (e.g., gold) on the sample.

A method of imaging will now be described. Elements of the system generally include samples which may include sections prepared for histological examination or cellular specimens prepared by smears or imprint preparation. Probes may comprise (i) Hematoxylin and eosin (H&E) or other transmission stains used for microscopic examination of cells or tissue in transmission microscopy, or antibody reagents with immunohistochemical reagents, or nucleic acid probes with chromogenic reporters. Probes can also comprise (ii) antibody reagents with fluorescence reporter molecules for detection of antigens, or nucleic acid probes with fluorescence reporters, or intercalating dyes. Included are applications in which at least one transmission die is used with a plurality of fluorescence reporters, each of which is applied to a separate slide in customary practice.

As described above, an AOTF-based spectral imaging microscopy system with transmission and epi-fluorescence capabilities is provided, such as system 600 shown in FIG. 6. As described above, disclosed systems provide low sidelobe levels of generally between −20 dB and −30 dB. Use of such a spectral imaging system allows the user to quantitatively resolve the multiple color fluorescence probes, as well as to eliminate artifactual contributions to the fluorescence images by the native fluorescence of the transmission stain.

In one embodiment of the invention, the sample comprises renal biopsy formalin-fixed, paraffin-embedded tissue sections, stained with H&E and, simultaneously, with 4 or more different antibodies conjugated to quantum dot or other fluorescence probes with center emission wavelengths ranging from 525 nm to 800 nm, for the detection of various disease-causing proteins in the glomerulus. The Imaging system can comprise an AOTF-based spectral imaging module, such as system 600 according to an embodiment of the invention shown in FIG. 6, and the image sensor comprises an electron-multiplying CCD camera, placed on top of an upright research-grade microscope capable of epi-fluorescence imaging.

Using subject matter disclosed herein applied to renal tissue, in one embodiment, a multiply-prepared slide would be placed onto the stage of the microscope and the AOTF module and be used to perform spectral imaging in both transmission and fluorescence, followed by a spectral classification analysis of the acquired images, resulting in the display of the H&E and the four (4) or more separate fluorescence images on the screen shortly thereafter for examination by the pathologist. Overlays of different combinations of images would facilitate the examination and subsequent diagnosis.

Embodiments of the invention will remove the need for a pathologist to require a separate tissue section or cytology specimen for each target to be examined with a fluorescence probe, and an additional specimen for the transmission stain examination. Examination of these numerous slides serve as multiple adjuncts for the pathologist in making the final diagnosis. The technique described herein allows all these tests to be performed on a single slide, thereby minimizing the amount of tissue required, avoiding artifacts resulting from the use of different parts of the tissue being used for each slide, and simplifying and speeding-up interpretation by the pathologist. Moreover, systems according to embodiments of the invention provide the ability to remove auto fluorescence.

EXAMPLES

It should be understood that the Examples described below are provided for illustrative purposes only and do not in any way define or in any way limit the scope of embodiments the invention.

Figure 7A:
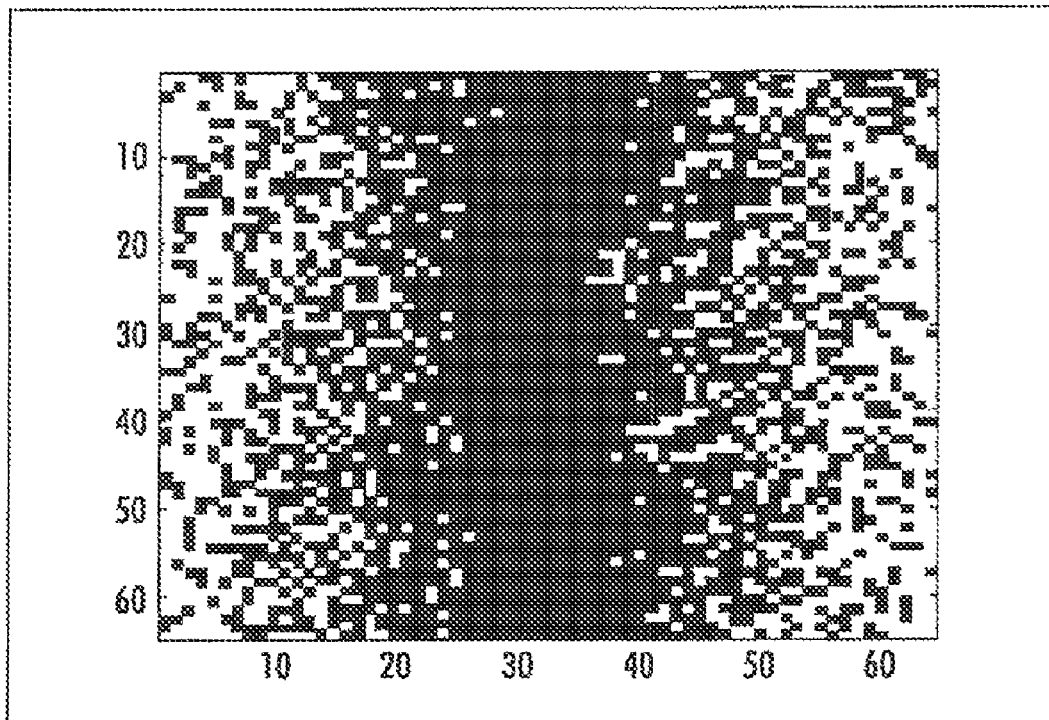
FIG. 7(a) shows a Gaussian weighting scheme for a transducer electrode based on 1-bit digitization of a Gaussian grey scale image, using error diffusion along a space filling fractal curve for an electrode pattern, according to an embodiment of the invention.

FIG. 7(a) shows a patterned electrode for a transducer derived from a Gaussian weighting scheme based on 1-bit digitization of a Gaussian grey scale image, using error diffusion along a space filling fractal curve, the Hilbert curve, according to an embodiment of the invention. The region occupied by the meandering space filling curve shown is a square of 64×64 pixels. In the AO crystal below the top electrode and its associated transducer (not shown), light moves from left to right. The black squares (pixels) representing the regions of top electrode metallization are not contiguous. The central columns are almost completely uninterrupted metal, with only a few isolated gaps or "holes", moving outwards from the center along a horizontal line (row) the metalled areas get progressively more sparse as one gets to the edges, making the probability of isolated metal "islands" rise as one moves towards the vertical edges.

As light moves from left to right it encounters regions of progressively higher acoustic intensity, as represented by the black (electroded) regions, with the center being the highest intensity. The average variation in this direction is Gaussian, truncated at the level where the tails fall to 10% of the peak value. The Inventors have found that this form of apodization function is generally satisfactory for most applications. In the orthogonal direction (the columns) the active transducer portion defined by the electrode pattern is uniform on average, such that there is no apodization in this direction. The electrode pattern shown in FIG. 7(a) is for illustrative purposes being only 64×64 pixels, and also being generally of no utility due to the difficulty in biasing the many non-contiguous electrode portions. This "raw" pattern is the result of digitizing a Gaussian grey-scale image in which each pixel contains a number between 0 and 1 representing the height of the Gaussian surface. The digitization is 1-bit digitization and is carried out with error diffusion around a 5th order Hilbert curve, as described in Peitgen (and references therein). The basic method is to start in one corner, advancing around the meandering Hilbert curve. At each pixel the following question is posed: "Is the numerical value of this pixel greater or less than 0.5?" If "greater", then a "1" (metal, represented by black squares) is put in that pixel, and the error is passed along the Hilbert curve to the next pixel. If "less" then a "0" is put in that pixel and the error transferred on to the next pixel. At each pixel it is the (value of the current pixel+error from last pixel digitization) which is digitized. This results in a pattern of black and white pixels such as shown in FIG. 7(a).

Figure 7B:
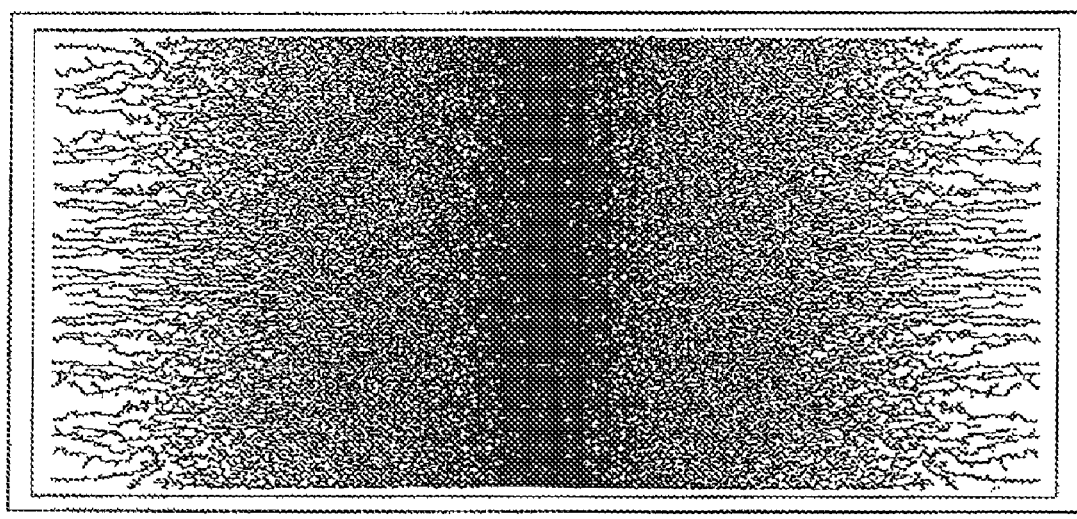
FIG. 7(b) shows a transducer electrode pattern derived from a higher order Hilbert curve, according to an embodiment of the invention.

The next step is to perturb or "shuffle" the columns of 7(a) in such a way that the total number of black squares in each column is unchanged (so as not to upset the Gaussian weighting) but they are moved about in a vertical direction so as to ensure that no diagonal connections between black squares or isolated black islands are left. The method actually employed by the Inventors starts this process in the center, where there is a nearly unbroken area of black, advancing to the left and right, column by column. At the start, there is very little to do as most of the black squares in a column are joined up anyway. The situation changes further from the center, because there are more isolated patches and even individual squares. The intermediate result of this procedure is not shown, but this procedure was repeated on a 256×256 array, to get the result shown in FIG. 7(b) which was the pattern actually used to generate the AO device for which results therefrom are shown in FIGS. 10-12. In FIG. 7(b) an additional step of "stretching" the pattern was performed in the horizontal direction by a factor of 2, because that gave the aspect ratio desired for the test device, a 2:1 length:width ratio. The precise value of this ratio in no way affects the method shown here, which is general.

The pattern was stretched using the following simple algorithm: For every pixel (square) in any row or column, another immediately adjacent square of the same type (black added to black, white added to white) was added in the same row to the right of it if we were on the right hand side of the vertical symmetry line, or on the left if on the left hand side.

A prototype apodized AO device according to an embodiment of the invention was fabricated, and tested. The AO device utilized the Hilbert curve defined transducer top electrode pattern shown in FIG. 7(b). In this pattern, the fundamental feature size (characteristic size of the fine structure; the finger widths) was about 10 µm.

The Hilbert curve defined electrode pattern apodized the acoustic field emitted by a LN transducer and reduced the sidelobes from −9.5 dB to −30 dB compared to a uniform (non-apodized) transducer top electrode in an acousto-optic tunable filter. Test conditions comprised an aperture of 12 mm square, placed between a pair of relay lenses of focal length 100 mm such that the light incident on the AOTF was substantially collimated. In this case, the order of the grid was increased from 64 to 256 and the columns were slightly re-arranged (keeping the number of black squares in any column constant) after the generation of the initial pattern in order that the whole electrode was contiguous, that it is all connected up electrically with no isolated islands of metal.

Figure 8A:
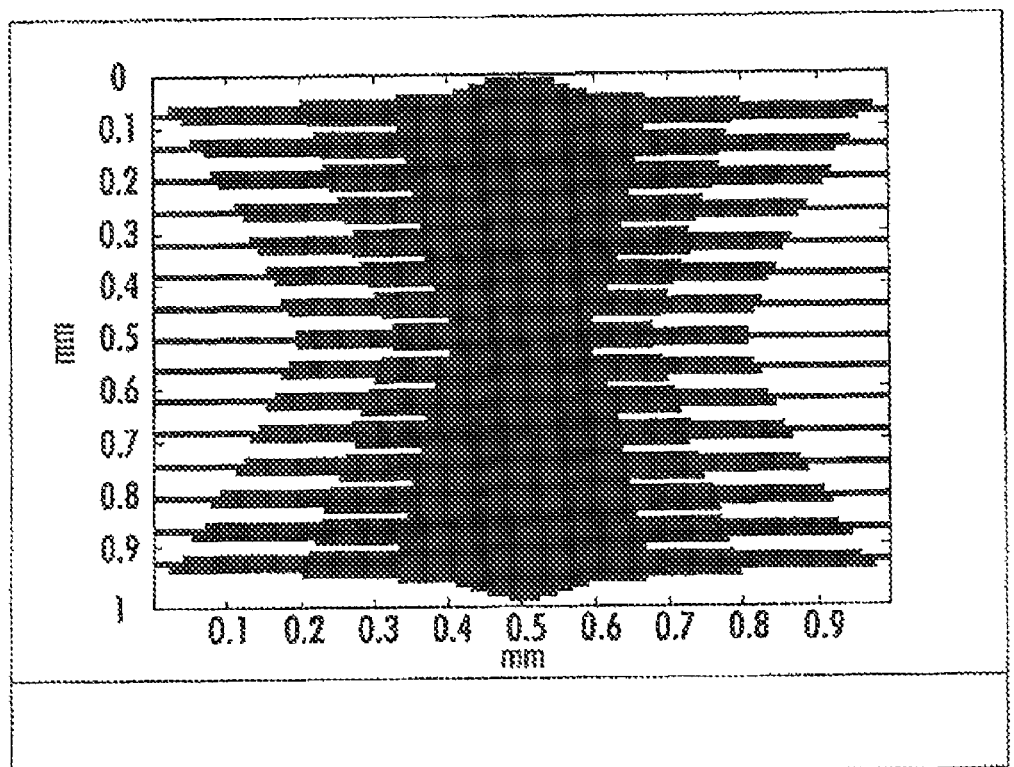
FIGS. 8(a) and (b) shows transducer electrode arrangements according to embodiments of the invention in which apodization is achieved by the introduction of metal top electrode patterns whose structure varies on a scale which is smaller than, or comparable to, the acoustic wavelength. From the center of the pattern there are progressively thinner and thinner "fingers" of metal, in order to approximate the Gaussian distribution when averaged over the columns.
Figure 8B:
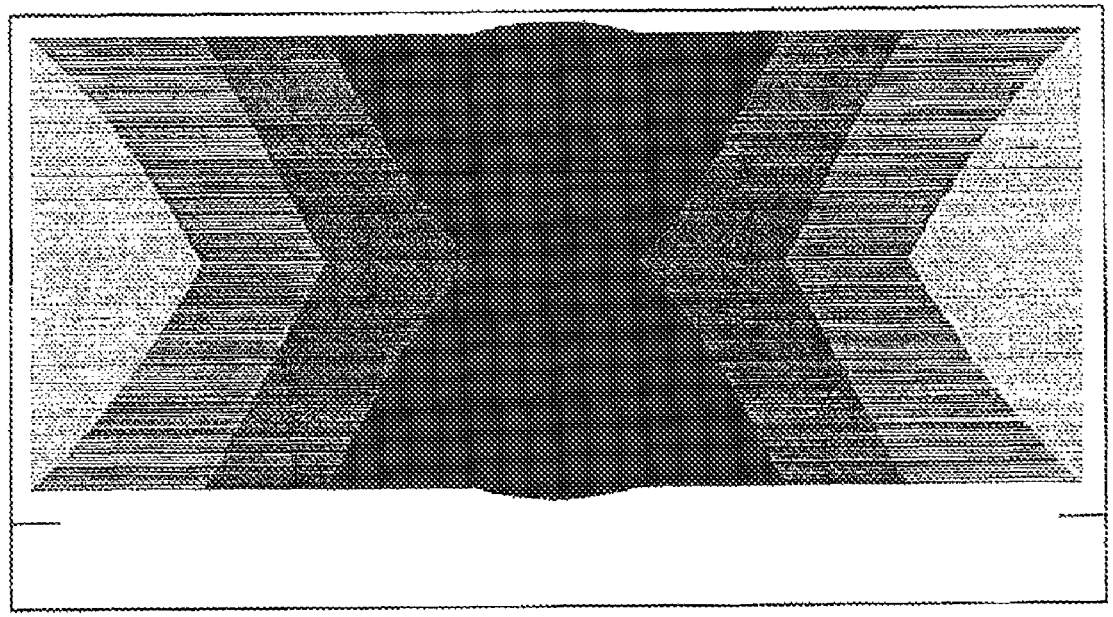

FIGS. 8(a) and (b) show electrode arrangements in which apodization is achieved by the introduction of metal patterns whose structure (finger width and finger spacing) varies on a scale which is smaller than, or comparable to, an acoustic wavelength, such as 10 µm. Such a pattern can be implemented using conventional photolithography, which can also be used to implement irregular features, such as curved or angled features. In the case shown, a more deterministic pattern was chosen where moving outwards from the center using progressively thinner and thinner "fingers" of metal approximates the Gaussian distribution when averaged over the columns. The central region is virtually uninterrupted metal, with the horizontal fingers becoming wide enough to merge together, while at the extreme left and right hand sides the fingers are at their narrowest in order to approximate to the tails of the Gaussian. The predominantly horizontal structure ensures that all the metal is contiguous from the start, and the extra step of joining up isolated metal islands is therefore not necessary. FIG. 8(a) shows a relatively coarse structure for the purposes of illustration, while FIG. 8(b) shows a much finer structure based on about 10 micron feature sizes, this latter is illustrative of a pattern that could be used in a practical device.

Figure 9A:
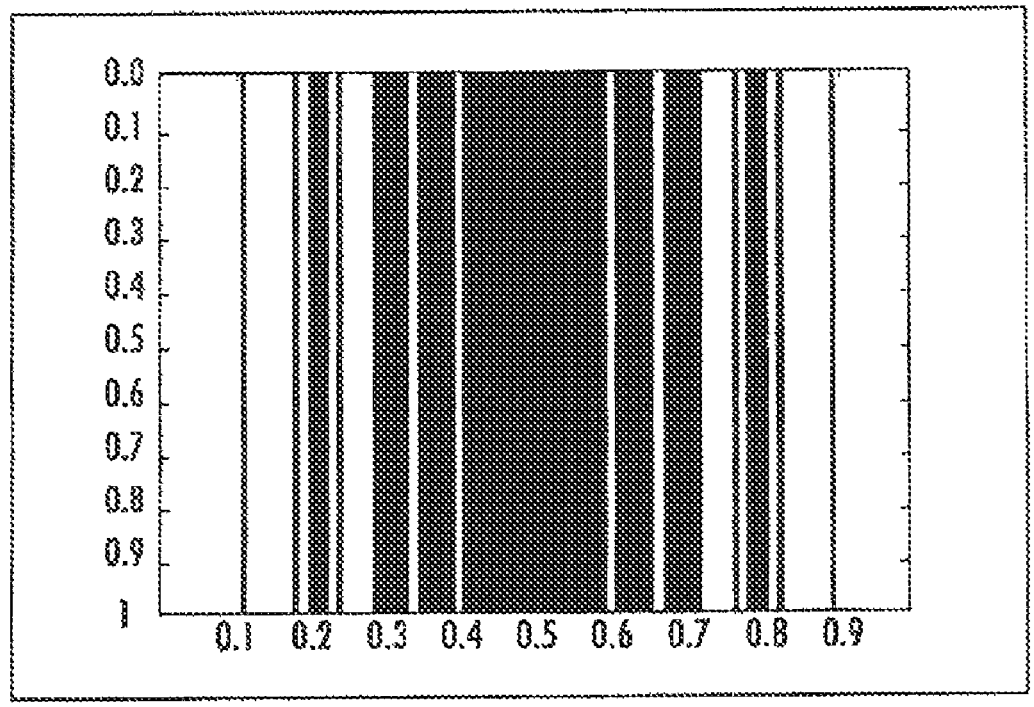
FIG. 9(a) shows another transducer electrode configuration for apodization according to an embodiment of the invention, where the number density of vertical fingers is adjusted in order to approximate a Gaussian apodization.
Figure 9B:
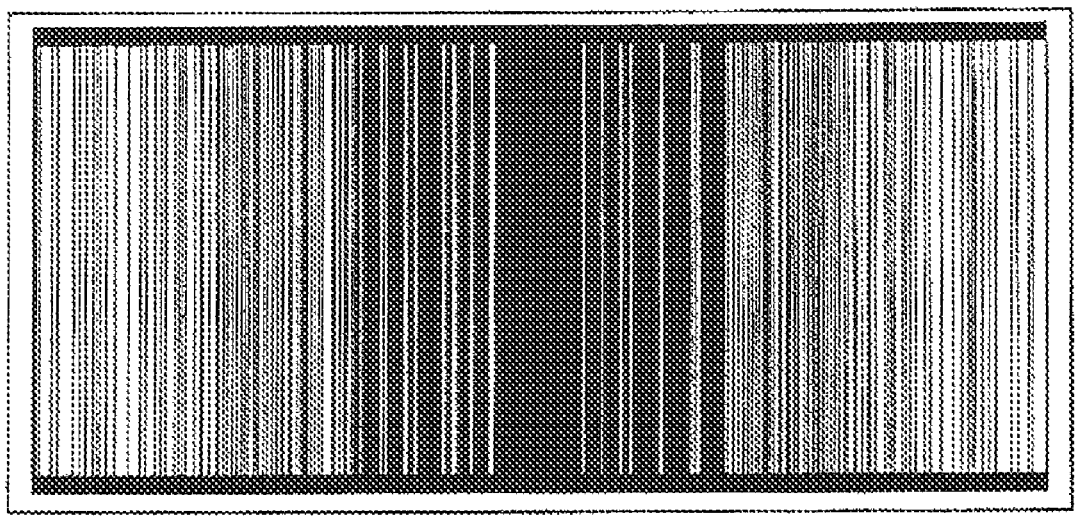
FIG. 9(b) shows another electrode pattern including fine structure according to an embodiment of the invention where the elementary width of the fingers shown are on the order of 5 to 10 microns. Near the pattern symmetry axis, the number density is high enough for the fingers to overlap and generate a continuous region. "Bus bars" are introduced at the top and bottom extremes of the rectangular area in order for the fingers to be electrically connected together.

FIGS. 9(a) and 9(b) shows alternate electrode configuration for an apodized transducers, according to embodiments of the invention. FIG. 9(a) is for illustrative purposes, while FIG. 9(b) is representative of a spatially fine pattern that could be used for a practical device. The number density of vertical fingers was adjusted in order to approximate a Gaussian apodization. The fine structuring condition according to this Disclosure is not present, which means that although the apodized transducer shown in FIG. 9(a) would function satisfactorily for a sonar transducer, it would not be suitable for most modern AO applications, such as for imaging.

FIG. 9(b) shows an electrode pattern including fine structure, according to an embodiment of the invention. The elementary width of the fingers shown are on the order of 5 to 10 microns. Near the pattern symmetry axis, the number density is high enough for the fingers to overlap and generate a continuous region. In this invention "bus bars" are introduced at the top and bottom extremes of the rectangular area in order for the fingers to be connected and form a contiguous electrode to facilitate biasing. Two bus bars are shown, but only one is generally necessary.

EXPERIMENTAL RESULTS

Figure 10A:
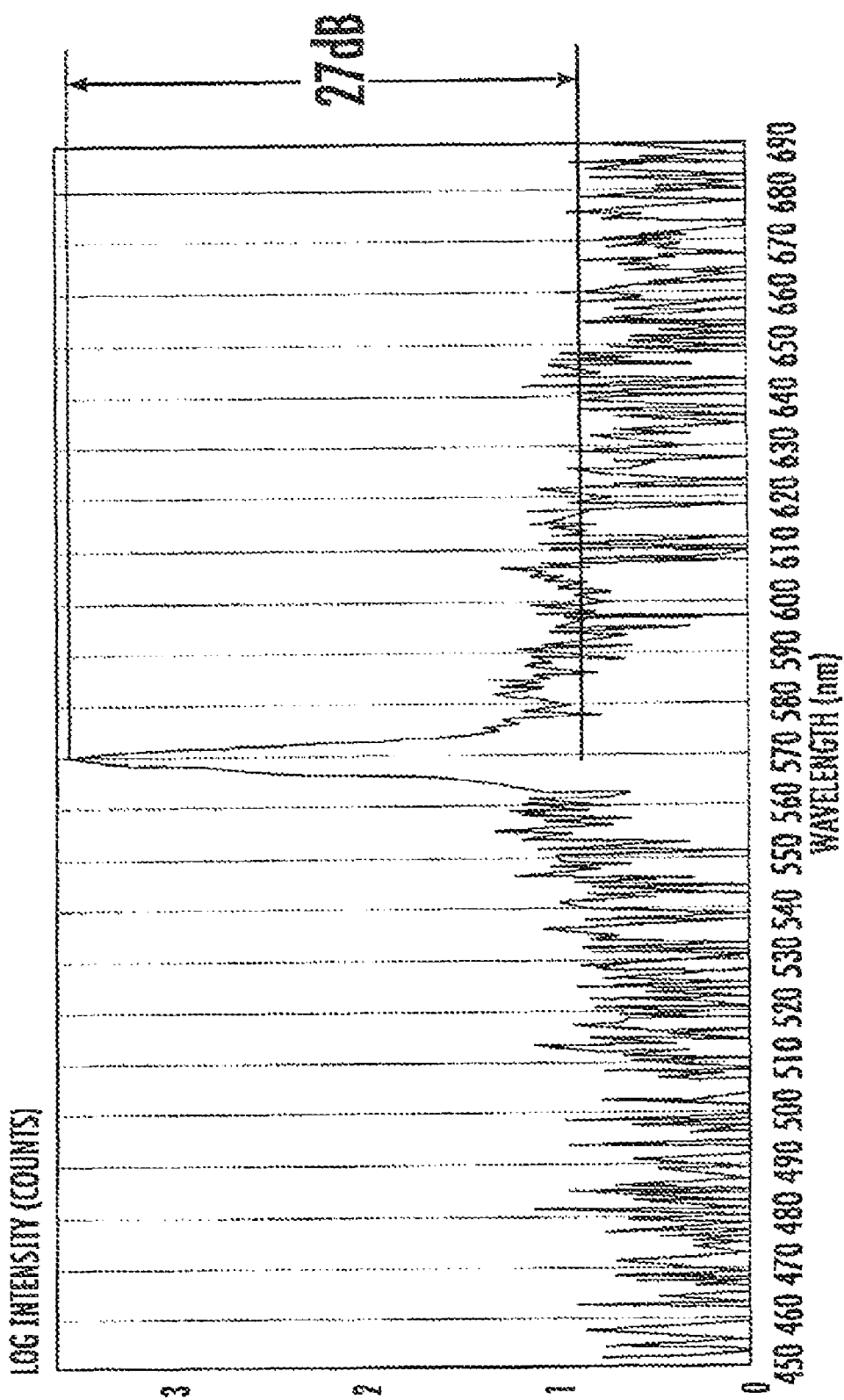
FIGS. 10(a), 11(a) and 12(a) show experimental results (at three (3) different operating optical wavelengths) according to an embodiment of the invention obtained from a fabricated AO device according to the invention including finely patterned electrode layer, while FIGS. 10(b), 11(b) and 12(b) compare the inventive results shown in FIGS. 10(a), 11(a) and 12(a) to a known AO device having eleven (11) separate transducer electrodes. Comparative results are displayed using solid curves for the inventive AO device while results from the known AO device are shown using dashed lines. Significantly lower side lobe levels are seen provided by the AO device according to an embodiment of the invention at each wavelength tested.
Figure 10B:
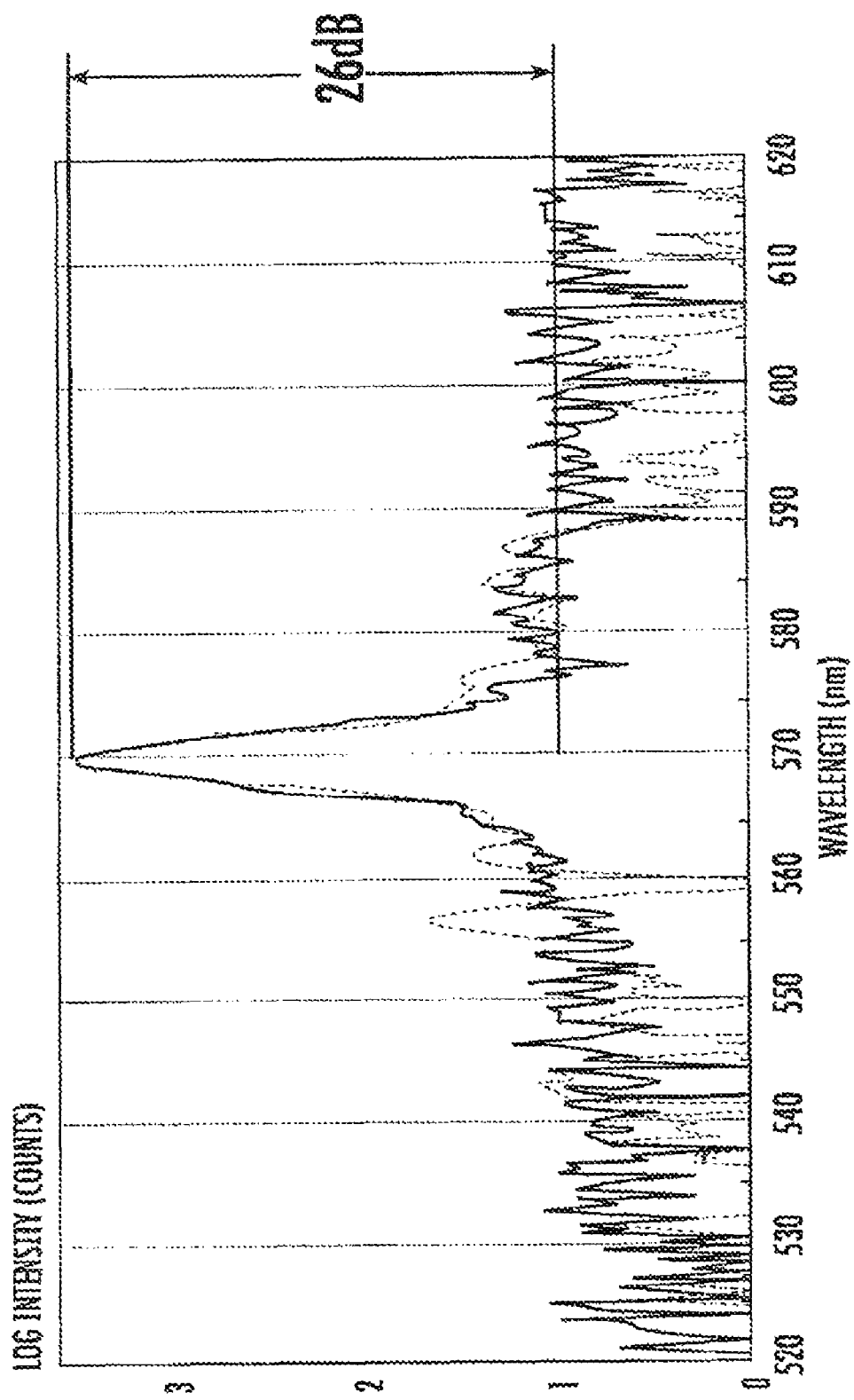
Figure 11A:
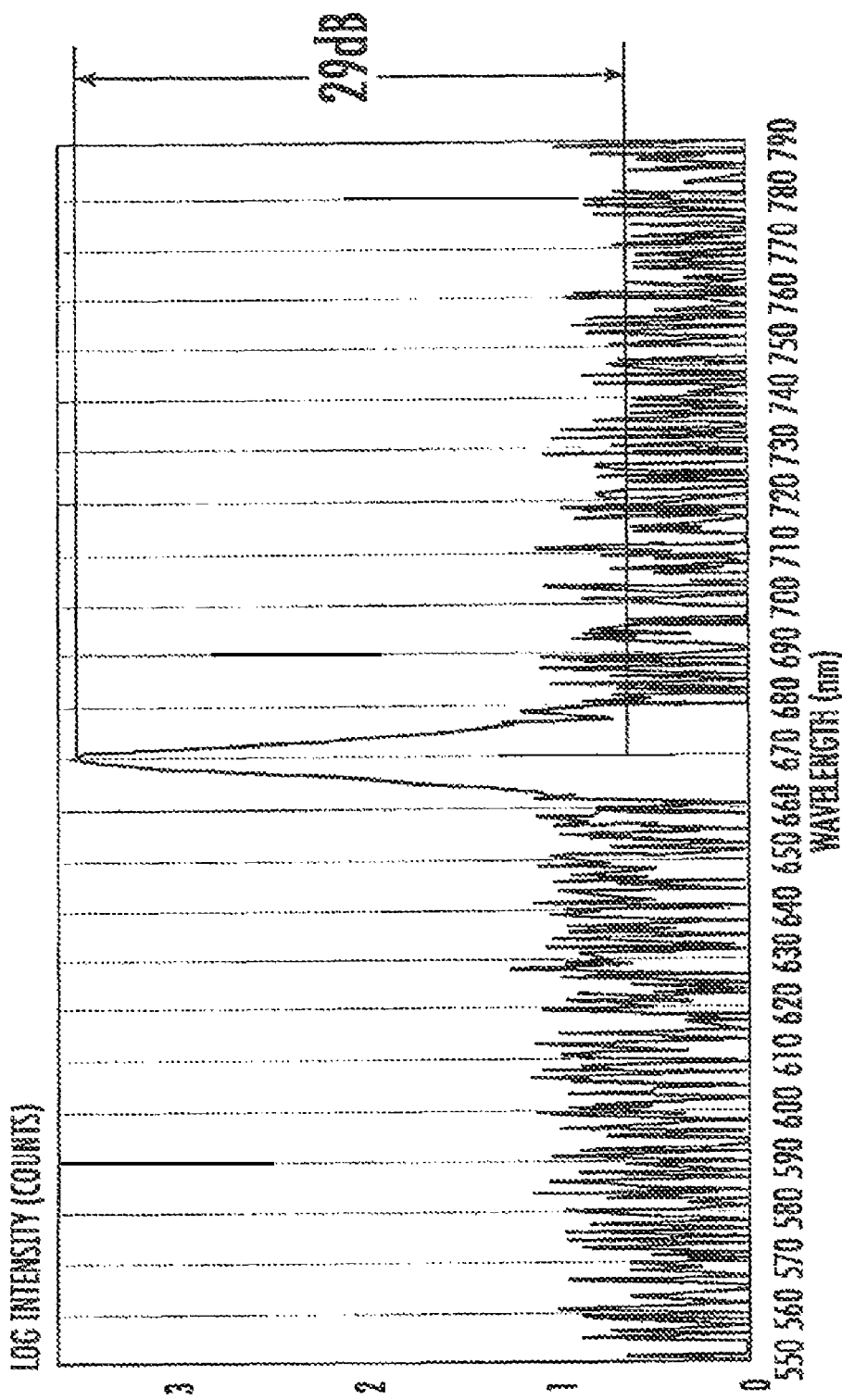
Figure 12A:
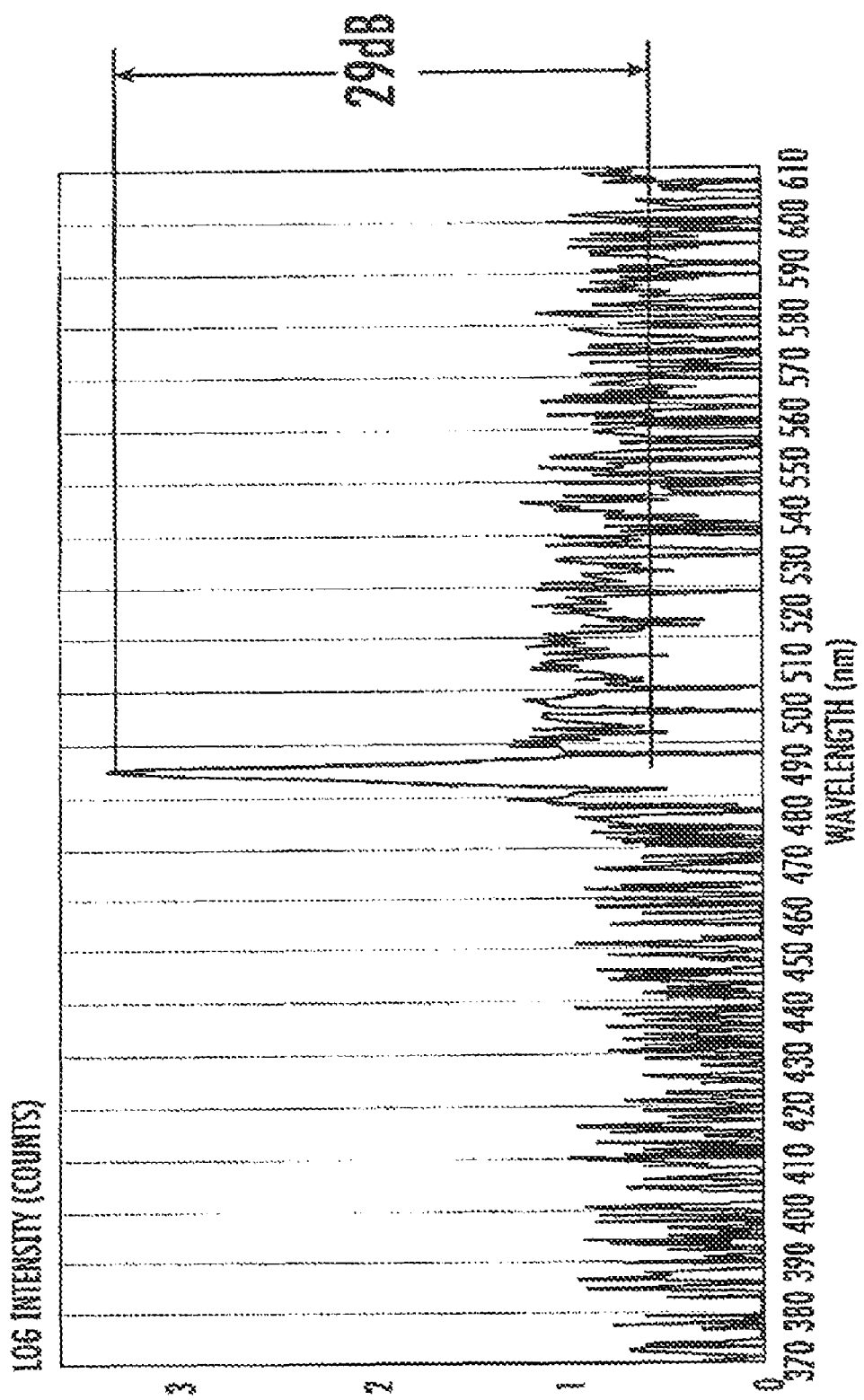
Figure 12B:
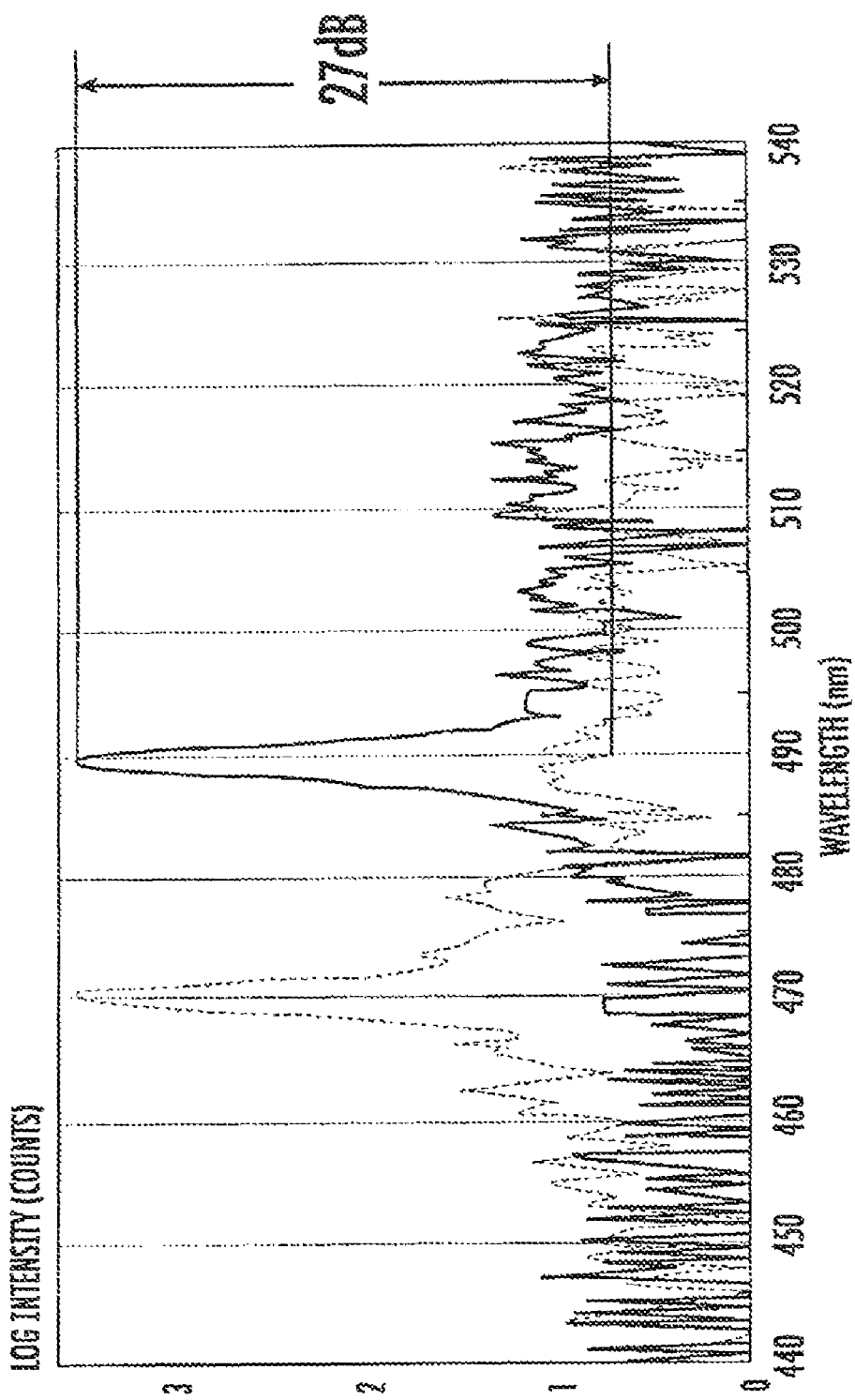

FIGS. 10(a), 11(a) and 12(a) show experimental results (at three (3) different operating optical wavelengths) obtained from a fabricated acousto-optic (AO) device according to an embodiment of the invention including finely patterned electrode layer, while FIGS. 10(b), 11(b) and 12(b) compare the inventive results shown in FIGS. 10(a), 11(a) and 12(a) to a known AO device having eleven (11) separate transducer electrodes. Comparative results are displayed using solid curves for the inventive device while results from the known AO device are shown using dashed lines. Significantly lower side lobe levels are seen provided by the AO device according to the invention at each wavelength tested. In addition to improved performance provided by devices disclosed herein, as noted above, the cost and complexity of such devices is significantly reduced as compared to known multi-electrode AO devices. For example, known AO devices require adjustment procedure needed to get all the transducer sub-elements operating substantially in phase over the whole tuning range, and operation requires a complicated and expensive bank of separate RF drivers.

The AOTF device according to the invention utilized the Hilbert curve defined (Gaussian) transducer top electrode pattern shown in FIG. 7(b). As noted above, in this pattern, the fundamental feature size (characteristic size of the fine structure; the finger widths and finger spacing) was about 5 to 10 µm.

Regarding the known AOTF device, the rectangular top electrode was divided up into eleven (11) electrically independent sub-electrodes. Each electrode was driven using a separate RF driver. In the arrangement used, each electrode segment was provided its own matching circuit and flexible cable connection to a multichannel RF driver, the latter containing all the RF drive electronics including the RF amplifiers. All the cables were closely matched in length to within a few mm and were adjusted to get all the transducer sub-elements operating substantially in phase over the whole tuning range.

The AOTF devices each had an aperture of 12 mm square optical aperture, o-ray incident, and was designed to have $\theta_i$=15.5 degrees as per FIG. 1. The acoustic angle, $\theta_a$ (again defined in FIG. 1 was 96.58 degrees. In each case the diffraction efficiency was adjusted to be a maximum, and in all cases this was approximately 88%. The temperature was room ambient, approx 23 degrees C. The AOTF devices were placed between a pair of relay lenses of focal length 100 mm such that the light incident on the AOTF was substantially collimated. The acoustic wavelength used was in the range from 5 to 10 microns. Measurements were performed at 3 wavelengths which were representative of the intended wavelength band (the visible) generally used by AOTFs, comprising 470/490 nm, 570 nm, 670 nm. For the test device, the acoustic wavelengths produced were approximately 5.5 microns for the 470/490 nm band 6.9 microns for the 570 nm band and 8.6 microns for the 670 nm band. If the experimental setup had allowed tuning to 800 nm, the acoustic wavelength would have been about 10.3 microns.

Referring now to FIG. 10(a), experimental results for an AOTF device according to an embodiment of the invention is shown at maximum efficiency at 490 nm. The intensity scale on the y-axis is a logarithmic scale, so that each increment represents 20 db. Side lobe levels are barely discernable over the noise level and appear to be about −27 dB from the peak shown. FIG. 10(b) shows the data from FIG. 10(a) (solid line) overlaid with data at 470 nm obtained using the known AOTF device having 11 separate transducer electrodes (dashed line). Sidelobe levels for the known AOTF device are seen to be readily identifiable above the noise level.

FIG. 11(a) shows experimental results for the inventive AOTF device at maximum efficiency at 570 nm. Sidelobe levels are again barely discernable and appear to be about −27 dB from the peak shown. FIG. 11(b) shows the data from FIG. 11(a) (solid line) overlaid with data at 570 nm obtained using the known AOTF device having 11 separate transducer electrodes (dashed line). Sidelobe levels for the known AO device are again seen to be readily identifiable above the noise level.

FIG. 12(a) shows experimental results for an AOTF device according to an embodiment of the invention at maximum efficiency at 670 nm. Sidelobe levels are again barely discernable and appear to be about −27 dB from the peak shown. FIG. 12(b) shows the data from FIG. 11(a) (solid line) overlaid with data at 670 nm obtained using the known AO device having 11 separate transducer electrodes (dashed line). Sidelobe levels for the known AO device are again seen to be readily identifiable above the noise level.

Applied to medical imaging, sidelobe suppression of generally at least −20 db provided by AOTFs according to embodiments of the invention permits a user to quantitatively resolve multiple color fluorescence probes, as well as to eliminate artifactual contributions to the fluorescence images by the native fluorescence of the transmission stain.

While various embodiments of the invention have been described above, it should be understood that they have been presented by way of example only, and not limitation. Numerous changes to the disclosed embodiments can be made in accordance with this Disclosure without departing from the spirit or scope of the invention. Thus, the breadth and scope of this Disclosure should not be limited by any of the above described embodiments. Rather, the scope of this Disclosure should be defined in accordance with the following claims and their equivalents.

Although embodiments of the invention has been illustrated and described with respect to one or more implementations, equivalent alterations and modifications will occur to others skilled in the art upon the reading and understanding of this specification and the annexed drawings. In addition, while a particular feature may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting to this Disclosure. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The Abstract of this Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the following claims.

We claim:

1. An imaging system, comprising:
a platform for placement of a sample or an animal to be imaged;
at least one excitation light source for irradiating said sample or said animal to stimulate a response comprising emissions at a plurality of different center wavelengths;
an acousto-optic tunable filter (AOTF) comprising:
a piezoelectric transducer crystal for emitting an acoustic wave having a ground electrode disposed on one side of said piezoelectric crystal;
a patterned electrode layer disposed on a side of said piezoelectric crystal opposite said ground electrode, said patterned electrode layer including a continuous region proximate to its center and a discontinuous region, a pattern in said discontinuous region comprising a plurality of spaced apart features electrically connected to said continuous region, and
an AO interaction crystal receiving said acoustic wave attached to said ground electrode or said patterned electrode layer, wherein feature sizes of said features in said pattern are sufficiently small to provide a fine structure far field condition for said acoustic wave in said AO interaction crystal underlying said discontinuous region beginning <10 mm measured from an interface between said piezoelectric crystal and said AO interaction crystal;
a radio frequencies (RF) power supply providing a variable RF frequency coupled across said electrodes for tuning a transmission wavelength of said AOTF, and
an image sensor coupled to receive said emissions transmitted by said AOTF.

2. The system of claim 1, wherein said tissue sample is on an optically transparent slide and includes at least one transmission stain, said system further comprising a broadband transmission source for obtaining transmission data from said transmission stain.

3. The system of claim 2, wherein said transmission stain comprises Hematoxylin and Eosin (H&E), a PAP stain, or an immunohistochemical stain.

4. The system of claim 3, wherein said immunohistochemical stain comprises Diaminobenzidine DAB.

5. The system of claim 1, wherein said tissue sample includes a plurality of different fluorescent stains having different respective emission wavelengths.

6. The system of claim 1, wherein said tissue sample is on an optically transparent slide and includes at least one transmission stain and at least one fluorescent stain, said system further comprising a broadband transmission source for obtaining transmission data from said transmission stain.

7. The system of claim 6, wherein said at least one fluorescent stain comprises a plurality of said fluorescent stains having different respective emission wavelengths.

* * * * *